United States Patent
Little et al.

(10) Patent No.: US 6,207,370 B1
(45) Date of Patent: Mar. 27, 2001

(54) DIAGNOSTICS BASED ON MASS SPECTROMETRIC DETECTION OF TRANSLATED TARGET POLYPEPTIDES

(75) Inventors: Daniel P. Little, La Jolla, CA (US); Scott Higgins, Paisley (GB); Hubert Köster, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 08/922,201

(22) Filed: Sep. 2, 1997

(51) Int. Cl.[7] ............................. C12Q 1/68; C12P 19/34
(52) U.S. Cl. ............................................ 435/6; 435/91.2
(58) Field of Search ........................ 435/6, 91.2, 7.1; 436/89, 94

(56) References Cited

U.S. PATENT DOCUMENTS

| | | | |
|---|---|---|---|
| 4,214,159 | 7/1980 | Hillenkamp et al. | 250/288 |
| 4,356,270 | 10/1982 | Itakura | 435/317 |
| 4,442,354 | 4/1984 | Hurst et al. | 250/281 |
| 4,683,194 | 7/1987 | Saiki et al. | 435/6 |
| 4,725,677 | 2/1988 | Köster et al. | 536/27 |
| 4,766,072 | 8/1988 | Jendrisak et al. | 435/91 |
| 4,778,993 | 10/1988 | Waugh | 250/287 |
| 4,920,264 | 4/1990 | Becker | 250/282 |
| 4,983,521 | 1/1991 | Lingappa et al. | 435/172.3 |
| 5,045,694 | 9/1991 | Beavis et al. | 250/287 |
| 5,062,935 | 11/1991 | Schlag et al. | 204/157.41 |
| 5,118,605 | 6/1992 | Urdea | 435/6 |
| 5,118,937 | 6/1992 | Hillenkamp et al. | 250/282 |
| 5,135,870 | 8/1992 | Williams et al. | 436/173 |
| 5,198,531 | 3/1993 | Webber et al. | 525/332.2 |
| 5,202,561 | 4/1993 | Giessmann et al. | 250/281 |
| 5,210,412 | 5/1993 | Levis et al. | 250/288 |
| 5,373,156 | 12/1994 | Franzen | 250/288 |
| 5,376,788 | 12/1994 | Standing et al. | 250/287 |
| 5,380,833 | 1/1995 | Urdea et al. | 536/22.1 |
| 5,381,008 | 1/1995 | Tanner et al. | 250/287 |
| 5,382,793 | 1/1995 | Weinberger et al. | 250/288 |
| 5,410,068 | 4/1995 | Coull et al. | 548/545 |
| 5,492,817 | 2/1996 | Thompson et al. | 435/68.1 |
| 5,503,980 | 4/1996 | Cantor | 435/6 |
| 5,510,613 | 4/1996 | Reilly et al. | 250/287 |
| 5,545,539 | 8/1996 | Miller | 435/91.2 |
| 5,547,835 | 8/1996 | Köster | 435/6 |
| 5,580,733 | 12/1996 | Levis et al. | 435/6 |
| 5,604,099 | 2/1997 | Erlich et al. | 435/6 |
| 5,605,798 | 2/1997 | Köster | 435/6 |
| 5,612,474 | 3/1997 | Patel | 536/27.14 |
| 5,622,824 | 4/1997 | Köster | 435/6 |
| 5,622,829 | 4/1997 | King et al. | 435/6 |
| 5,625,184 | 4/1997 | Vestal et al. | 250/287 |
| 5,627,369 | 5/1997 | Vestal et al. | 250/287 |
| 5,628,184 | 5/1997 | Santos | 60/39.281 |
| 5,631,134 | 5/1997 | Cantor | 435/6 |
| 5,641,959 | 6/1997 | Holle et al. | 250/287 |
| 5,643,722 | 7/1997 | Rothschild et al. | 435/6 |
| 5,643,798 | 7/1997 | Beavis et al. | 436/94 |
| 5,654,545 | 8/1997 | Holle et al. | 250/287 |
| 5,663,242 | 9/1997 | Ghosh et al. | 525/329.4 |
| 5,670,322 | 9/1997 | Eggers et al. | 435/6 |
| 5,670,381 | 9/1997 | Jou et al. | 436/518 |
| 5,677,195 | 10/1997 | Winkler et al. | 436/518 |
| 5,691,141 | 11/1997 | Köster | 435/6 |
| 5,700,642 | 12/1997 | Monforte et al. | 435/6 |
| 5,742,049 | 4/1998 | Holle et al. | 250/282 |
| 5,760,393 | 6/1998 | Vestal et al. | 250/282 |
| 5,777,324 | 7/1998 | Hillenkamp | 250/288 |
| 5,777,325 | 7/1998 | Weinberger et al. | 250/287 |
| 5,792,664 | 8/1998 | Chait et al. | 436/89 |
| 5,795,714 | 8/1998 | Cantor et al. | 435/6 |
| 5,830,655 | 11/1998 | Monforte et al. | 435/6 |
| 5,864,137 | 1/1999 | Becker et al. | 250/287 |
| 5,869,242 | 2/1999 | Kamb | 435/6 |

FOREIGN PATENT DOCUMENTS

| | | |
|---|---|---|
| 0269250 | 6/1988 | (EP) . |
| 0655501 | 5/1995 | (EP) . |
| WO 90/14148 | 11/1990 | (WO) . |
| WO 92/10092 | 6/1992 | (WO) . |
| 9324834 | 12/1993 | (WO) . |
| WO 94/00562 | 1/1994 | (WO) . |
| 9428418 | 12/1994 | (WO) . |
| 9525737 | 9/1995 | (WO) . |
| 0683234 | 11/1995 | (WO) . |
| 9531429 | 11/1995 | (WO) . |
| WO 96/36732 | 11/1996 | (WO) . |
| 9719110 | 5/1997 | (WO) . |
| WO 97/43617 | 11/1997 | (WO) . |
| WO 97/49993 | 12/1997 | (WO) . |
| WO 98/32876 | 7/1998 | (WO) . |

OTHER PUBLICATIONS

Belanger et al., Molecular mass and carbohydrate structure of porstate specific antigen: studies for establishment of an international PSA standard, *Prostate*, 27(4); 187–197 (1995).

Haag et al., Rapid identification and speciation of Haemophilus bacteria by matrix–assisted laser desorption/ionization time–of–flight mass spectrometry, *J. of Mass Spectrometry*, 33(8): 750–756 (1988).

(List continued on next page.)

*Primary Examiner*—Eggerton A. Campbell
(74) *Attorney, Agent, or Firm*—Stephanie L. Seidman; Heller Ehrman White & McAuliffe LLP

(57) ABSTRACT

The invention provides a means of detecting and identifying mutations in a genetic region, and a means of quantifying the number of repeat units in, for example, a trinucleotide repeat, by transcription/translation of the genetic region into a target polypeptide. The method requires neither radioisotopic nor fluorescent labeling of the target polypeptide. In particular, the invention is based on mass spectrometric determination of the mass of the encoded target polypeptide and comparison of the mass of the polypeptide with its own expected mass or with the mass of a polypeptide of known identity. Depending on the target polypeptide to be identified, the processes can be used, for example, to diagnose a genetic disease or chromosomal abnormality; a predisposition to a disease or condition, infection by a pathogenic organism, or for determining identity or heredity.

24 Claims, 1 Drawing Sheet

OTHER PUBLICATIONS

Krishnamurthy and Ross, Rapid identification of bacteria by direct matrix assisted laser desorption/ionization mass spectrmetric analysis of whole cells, *Rapid Comm in Mass Spectrometry*, 10(15): 1993–1996(1996).

Krishnamurthy et al., Biomolecules and mass spectroscopy, *J. of Natural Toxins*, 6(2): 121–162 (1997).

Tas et al., Characterization of virus infected cell cultures by pyrolysis/direct chemical ionization and mass spectrometry, *Biomed and Environ Mass Spect*, 18(9): 757–770 (1989).

Welham et al., The rapid identification of intact microorganisms by matrix–assisted laser desorption/ionization time–of–flight masss spectrometry, *Pharmacy and Pharmacology Comm.*, 4(2): 81–87 (1998).

Anderson, et al., Preparation of a cell–free protein–synthesizing system from wheat germ, *Meth. Enzymology 101*, :635–644 (19830.

Andersen, et al., Electrospray ionization and matrix assisted laser desorption/ionization mass spectrometry: Powerful analytical tools in recombinant protein chemistry. *Nature Biotech.*, 14:449–457 (1996).

Ardrey, Electrospray mass spectrometry, *Spectroscopy Europe*, 4:10–18 (1992).

Barany, Genetic disease detection and DNA amplification using cloned thermostable ligase, *Proc. Natl. Acad. Sci. USA*, 88:189–193 (1991).

Batra, et al., Insertion and constant region domains of human IgG$_1$ into CD4–PEG40 increases its plasma half–life, *Molec. Immunol.*, 30:379–386 (1993).

Beckmann and Weber, "Survey of human and rat microsatellites", *Genomics*, 12:627–631 (1992).

Brennan and Matthews, Hb Auckland [α87 (F8)His→Asn]: A new mutation of the proximal histidine identified by electrospray mass spectrometry. *Hemoglobin*, 21:393–403 (1997).

Brook, et al., Molecular basis of myotonic dystrophy: Expansion of a trinuleotide (CTG) repat at the 3'end of a transcript encoding a protein kinase family member, *Cell 68*, :799–808 (1992).

Chakrabarti, et al., Sequence of simian immunodeficiency virus from macaques and its relationship to other human simian retroviruses, *Nature328*, :543–547 (1987).

Cooper and Krawczak, *Human Gene Mutaion*, Bios Scientific Publishers (1993).

Covey, et al., The determination of protein, oligonucleotide and peptide molecular weights by ion–spray mass spectrometry. *Rapid Comm. Mass Spec.*, 2:249–565 (1988).

Crain, Mass spectrometric techniques in nucleic acid research, *Mass. Spec. Rev. 9*, :505–554 (1990).

Ecker and Crooke, Combinatorial drug discovery: Which methdos will produce the greatest value ?*Bio/Technology 13*, :351–360 (1995).

Edwards, et al., Pentanucleotide repeat length polymorphism at the human CD4 locus, *Nucleic Aicids Res.*, 19:4791 (1991).

Ellison and Hochstrasser, Epitope–tagged ubiquitin, *J. Biol. Chem. 266*:21150–21157 (1991).

Erickson and Blobel, "Cell–free translation of messenger RNA in a wheat germ system", *Meth. Enzymol. 96*, :38–50 (1983).

Falick, et al., Tandem masss spectrometry in the clinical analysis of variant hemoglobins. *Rapid Comm. Mass Spec.* 4:396–400 (1990).

Fey, et al., Proteome analysis of *Saccharomyces cervisiae*: A methodological outline. *Electrophoresis 18*: 1361–1372 (1997).

Fu, et al., Variation of the CGG repat at the Fragile X site results in genetic instability: Resolution of the Sherman Paradox, *Cell 67*, :1047–1058 (1991).

Gildea et al., A versatile acid–labile linker for modification of synthetic biomolecules, *Tetrahedron Lett. 31*, :7095–7098 (1998).

Greene and Wuts, *Protective Groups in Organic Synthesis, 2nd Ed.,*, John Wiley & Sons, Inc., New York (1991).

Gust et al., Taxonomic classification of Hepatitids A virus, *Invervirology 20*, :1–7 (1983).

Guyader et al., Genome organization and transactivation of the human immunodeficienc7y virus type 2, *Nature 326*, :662–669 (1987).

Higuchi, et al., Kinetic PCR analysis: Real–time monitoring of DNA amplification reactions, *Bio/Technology 11*, :1026–1030 (1987).

Hillenkanp, et al., Matrix assisted UV–laser desopriton/ionizatioin: A new approach to mass spectrmetry of large biomolecules, In Burlinghame and McCloskey (eds.), *Biological Mass Spectrometry*, Elsevier Science Publishers B.V., Amsterdam (1990).

Hirst, et al., Generation of a large combinatorial library of the immunoglobulin repertoire in phage lambda, *Science 246*, :1275–1281 (1989).

Huse, et al., Generation oa a large combinatorial library of the immunoglobulin repertoire in phage lambda, *Science 246*, :1275–1281 (1989).

Jellinek, et al., Potent 2'–amino–2'–deoxypyrimidine RNA inhibitors of basic fibroblast growth factor, *Biochemistry*, 54, :11363–11372 (1995).

Ji, et al., Two–dimensional electrophoretic analysis of proteins expressed by normal and cancerous human crypts: Application of mass spectrometry to peptide–mass fingerprinting. *Electrophoresis*, 15: 391–405 (1994).

Juhasz, et al., Applications of delayed extraction matrix–assisted lasewr desorption inoizatio time–of–flight mass spectrometry to oligonucleotide analysis, *Anal. Chem. 68*, :941–946 (1996).

Kremer et al., Mapping of DNA instability at the Fragile X to a trinucleotide repeat sequence p(CCG)n, *Science 252*, :1711–1714 (1991).

Kussmann, et al., Matrix–assisted laser desorption/ionization mass spectrometry sample preparation techniques designed for various peptide and protein analytes, *J. Mass. Spec. 32*, :593–601 (1997).

La Spada et al., Androgen receptor gene mutatin in X–linked spinal and bulbar muscular atrophy, *Nature 352*: 77–79 (1991).

Leznoff, The use of insoluble polymer supports in general organic synthesis, *Accts. Chem. Res. 11*, :327–333 (1978).

Li, et al., Analysis of single mammalian cell lysates by mass spectrometry, *J. Am. Chem. Soc. 118*, :11662–11663 (1996).

Lin, et al., Modified RNA sequence pools for in vitro selection, *Nucleic Acids Res. 22*, :5229–5234 (1994).

Mahadevan, et al., Myotonic dystrophy mutation: An unstable CTG repeat in the 3'untranslated region of the gene, *Science 255*, :1253–1255 (1992).

McCray and Trentham, Properties and uses of photoreactive caged compounds, *Ann. Rev. Biophys. Biophys. Chem. 18*, :239–270 (1992).

Miyazaki, et al., The first Japanese case of Hb Santa Ana, an unstable abnormal hemoglobin, identified rapidly by electrospray ionization mass spectrometry. *Internal Medicine 36*, :365–370 (1997).

Murray, "DNA sequencing by masss spectrometry", *J. Mass. Spect. 31*, :1203–1215 (1996).

Narang et al., Improved phospotriester method for the synthesis of fragments, *Meth. Enzymol. 68*, :90–98 (1979).

Pagratis, et al., Potent 2'–amino–. and 2'–fluoro–2'–deoxyribonucleotide RNA inhibitors of keratinocyte growth factory, *Nature Biotech.*, 15:68–73 (1997).

Ploos van Amstel and Reitsma, Tetranucleotide repeat polymorphism in the vWF gene, *Nucleic Acids Res.*, 18:4957 (1990).

Polymeropoulos, et al., Dinucleotide repeat polymorphism at the int–2 proto–oncogene locus (INT2), *Nucleic Acids Res.*, 18: 7468 (1990).

Polymeropoulos, et al., Trinucleotide repeat polymorphism at the human pancreatic phospholipase A–2 gene (PLA–2), *Nucleic Acids Res.*, 18:7468 (1990).

Polymeropoulos, et al., Tetranucleotide repeat polymorphism at the human c–fes/fps proto/oncogene (FES), *Nucleic Acids Res.*, 19:4018 (1991).

Polymeropoulos, et al., Dinucleotide repeat polymorphism in the human CTLA4 gene, *Nucleic Acids Res.*, 19:4018 (1991).

Raftery, et al., Characterization of a mutant recombinant S100 protein using electrospray ionization mass spectrometry. *Rapid Comm. Mass Spec.*, 11:405–409 (1997).

Ratner, et al., "Complete nucleotide sequence of the AIDS virus, HTLV–III", *Nature 313*, :277–284.

Rink, "Solid–phase synthesis of protected peptide fragments using a trialkoxy–diphenyl–methlester resin", *Tetrahedron Lett. 28*, :3787–3790 (1987).

Roberts, et al, "Efficient translation of tobacco mosaic virus RNA and rabbit globin 9S RNA in a cell–free system from commercial wheat germ", *Proc. Nat. Acad. Sci, USA 70*, :2330–2334 (1973).

Schram, "Mass spectrometry of nucleic acid and compnents", *Biomed Appl of Mass Spect 34*, :203–287.

Seong, et al., "*Escherichia coli*, formylmethionine tRNA: mutations in GGG CCC sequence conserved in anticodon stem of initiator tRNS affect initiation of protein synthesis and confirmation of anticodon loop", *Proc. Natl. Acad. Sci. USA 84*, :334–338.

Smith, et al., New developments in biochemical mass spectrometry: Electrospray Ionization, *Anal. Chem. 62*, :882–889 (1990).

Spirin et al., "A continuous cell–free translation system capable of producing polypeptides in high yield", *Science 242*, :1162–1164 (1988).

Tam et al., Biological availability and nuclease resistance extend the in vitro activity of a phosphorothioate–3 'hydroxypropylamine oligonucleotide, *Nucleic Acids Res.*, 22:977–986 (1994).

Thompson and Thompson (eds.), *Genetics in Medicine, 4th Ed.*, W. B. Saunder Co., Philadelphia (1986).

Valaskovic, et al., Attomole–sensitivity electrospray source for large–molecule mass spectrometry, *Anal. Chem. 67*, :3802–3805 (1995).

Valaskovic, et al., Attomole protein characterization by capillary electrophoresis–mass spectrometry, *Science 273*, :1199–1202 (1996).

von Eckardstein, et al., Structural analysis of human apolipoprotein A–I variants. *J. Biol. Chem. 265*, :8610–8617 (1990).

Vorm, et al.., Improved resolution and very high sensitivity in MALDI TOF of matrix surfaces made by fast evaporation, *Anal. Chem. 66*, :3281–3287 (1994).

Wain–Hobson, et al., "Nucleotide sequence of the AIDS virus, LAV", *Anal. Chem. 66*, :3281–3287 (1994).

Walker, et al., Multiplex strand displacement amplification (SDA) and detection of DNA sequences from *Mycobacterium tuberculosis*, and other mycobacteria, *Nucleic Acids Res. 22*, :2670–2677 (1994).

Ward, et al., Binding activities of a repertoire of single immunoglobulin variable domains secreted from *Escherichia coli*, *Nature 341*, :544–546 (1989).

Weber, et al., Abundant class of human DNA polymorphisms which can be typed using the polymerase chain reaction, *Am. J. Hum. Genet. 44*, :388–396 (1989).

Yamashita and Fenn, Electrospray ion source. Another variation on the free–jet theme, *J. Phyus. Chem. 88*, :4451–4459 (1984).

Yates, III, Mass spectrometry and the age of the proteome *J. Mass. Spec. 33*, : 1–19 (1998).

Derwent Abstract for PCT WO 97/49993, *Brenner, et al.* , Diagnostic detection od pathogenic point mutation(s) –in e.g. heart disease, by protein analysis of expression of prepared biopisies.

5'd (GAC TTT ACT TGT ACG TGC *ATA ATA CCA CTC ACT ATA GGG AGA* CTG
AAC ATG GGC AGT CTG AGC CAG CAG ACG CCG GGA CAC AAG GCT GAG CAG CAG
CAG CAG CAG CAG *CAG CAG CAG* CAC CAT CAG CAG CAT CCG GGC CTC ATC
ACC CCG GGT CCC CAG CCC AGC AGA ACG AGT ACG TCC ACA TTT
CAA GTT CAT CAT CAT CAT CAT CAT TGA GAA TCA) -3' (SEQ ID NO. 8)

B

MGSLSQTPGH KAEQQQQQQ QQQQQHQHQQ QQQQQQQHL
SRAPGLITPG PPGQPSRTST STGQVHHHHHH H (SEQ ID NO. 9)

DIAGNOSTICS BASED ON MASS SPECTROMETRIC DETECTION OF TRANSLATED TARGET POLYPEPTIDES

BACKGROUND OF THE INVENTION

In recent years, the molecular biology of a number of human genetic diseases has been elucidated by the application of recombinant DNA technology. More than 3000 diseases are currently known to be of genetic origin (Human Genome Mutations, D. N. Cooper and M. Krawczak, BIOS Publishers, 1993). These include hemophilias, thalassemias, Duchenne Muscular Dystrophy (DMD), Huntington's Disease (HD), Alzheimer's Disease, Cystic Fibrosis (CF), and various cancers, e.g., breast cancer. In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klinefelter's Syndrome (XXY).

Other genetic diseases are caused by an abnormal number of trinucleotide repeats in a gene. These diseases include Huntington's disease, prostate cancer, Spinal Cerebellar Ataxia (SCA), Fragile X syndrome (Kremer et al., Science 252:1711–14 (1991); Fu et al., Cell 67:1047–58 (1991); Hirst et al. J. Med. Genet. 28:824–29 (1991)), Myotonic Dystrophy (MD) type I ( Mahadevan et al., Science 255:1253–55 (1992); Brook et al., Cell 68:799–808 (1992)), Kennedy's disease, also termed Spinal and Bulbar Muscular Atrophy (La Spada et al., Nature 352:77–79 (1991)), Machado-Joseph disease, Dentatorubral and Pallidolyusian Atrophy. The aberrant number of triplet repeats can be located in any region of a gene, including the coding regions, non-coding regions of exons, introns, and promoter. In certain of these diseases, e.g., prostate cancer, the number of tiplet repeats is positively correlated with prognosis of the disease. All available evidence suggests that amplification of a tri-nucleotide repeat is involved in the molecular pathology in each of these disorders. Although some of these trinucleotide repeats appear to be in non-coding DNA, they clearly are involved with perturbations of genomic regions that ultimately affect gene expression. Perturbations of various di-and tri-nucleotide repeats resulting from somatic mutation in tumor cells could also affect gene expression and/or gene regulation.

Further, there is growing evidence that certain DNA sequences may predispose an individual to any of a number of other diseases such as diabetes, arteriosclerosis, obesity, various autoimmune diseases and cancer (e.g., colorectal, breast, ovarian, lung). The knowledge of the genetic lesion causing or contributing to a genetic disease allows one to predict whether a person has or is at risk of developing a disease or condition and also, at least in some cases, to determine the prognosis of the disease.

Furthermore, numerous genes have polymorphic regions. Since individuals have any one of several allelic variants of a polymorphic region, individuals can be identified based on the type of allelic variants of polymorphic regions of genes. This can be used, e.g., for forensic purposes. In other situations, it is crucial to know the identity of allelic variants that an individual has. For example, allelic differences in certain genes, e.g., major histocompatibility complex (MHC) genes are involved in graft rejection or graft versus host disease in bone marrow transplantation. Accordingly, it is highly desirable to develop rapid, sensitive, and accurate methods for determining the identity of allelic variants of polymorphic regions of genes and/or genetic lesions.

Several methods for detecting the identity of allelic variants or genetic lesions are currently in use. For example, the identity of an allelic variant or the presence of a genetic lesion can be determined by comparing the mobility of an amplified nucleic acid fragment with a known standard by gel electrophoresis, or by hybridization with a probe, which is complementary to the sequence to be identified. Identification, however, can only be accomplished if the nucleic acid fragment is labeled with a sensitive reporter function (e.g. radioactive ($^{32}$P, $^{35}$S), fluorescent or chemiluminescent). However, radioactive labels can be hazardous and the signals they produce decay over time. Non-isotopic labels (e.g. fluorescent) suffer from a lack of sensitivity and fading of the signal when high intensity lasers are being used. Additionally, performing labeling, electrophoresis and subsequent detection are laborious, time-consuming and error-prone procedures. Electrophoresis is particularly error-prone, since the size or the molecular weight of the nucleic acid cannot be directly correlated to the mobility in the gel matrix. It is known that sequence specific effects, secondary structures and interactions with the gel matrix are causing artefacts.

Other detection methods involve mass spectrometry. In general, mass spectrometry provides a means of "weighing" individual molecules by ionizing the molecules in vacuo and making them "fly" by volatilization. Under the influence of electric and/or magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collisionally activated dissociation (CAD). The fragmentation pattem/pathway very often allows the derivation of detailed structural information. Many applications of mass spectrometric methods are known in the art, particularly in the biosciences, and can be found summarized in Methods in Enzymology, Vol. 193: "Mass Spectrometry" (J. A. McCloskey, editor), 1990, Academic Press, New York; McLaffery et al., (1994) Acc. Chem. Res. 27:397–386; Chait & Kent (1992) Science 257:1885–1894; Siuzdak, (1994) Proc. Natl. Acad. Sci. USA 91:11290–11297.

Due to the apparent analytical advantages of mass spectrometry in providing high detection sensitivity, accuracy of mass measurements, detailed structural information by CAD in conjunction with an MS/MS configuration and speed, as well as on-line data transfer to a computer, there has been considerable interest in the use of mass spectrometry for the structural analysis of nucleic acids. Recent reviews summarizing this field include K. H. Schram, "Mass Spectrometry of Nucleic Acid Components, Biomedical Applications of Mass Spectrometry" 34, 203–287 (1990); P. F. Crain, "Mass Spectrometric Techniques in Nucleic Acid Research," Mass Spectrometry Reviews 9, 505–554 (1990); and Murray, K. (1996) J. Mass. Spectrom. Rev. 31:1203; and Nordhoff et al. (1997) J. Mass Spectrom. 15:67.

However, analysis of DNA molecules by mass spectrometry has certain limitations, such as the fact that nucleic acids are very polar biopolymers that are very difficult to volatilize.

SUMMARY OF THE INVENTION

In general, the invention provides processes and kits for determining the identity of a target polypeptide. The processes of the invention, essentially comprise the steps of (i) obtaining a target polypeptide; (ii) determining the molecular mass of the target polypeptide by mass spectrometry; and (iii) comparing the molecular mass of the target polypeptide with the molecular mass of a reference polypeptide of known identity, to thereby determine the identity of the target polypeptide. In a preferred embodiment of the invention, step (i) comprises transcribing a nucleic acid encoding the target polypeptide into RNA and translating the RNA into the target polypeptide. In an even more preferred embodiment, the process further comprises a step of amplifying the nucleic acid prior to step (i) or (ii), such as by polymerase chain reaction using a forward and a reverse primer, for example. The forward primer preferably comprises an RNA polymerase promoter, such as an SP6 promoter, T3 promoter, or T7 promoter. Preferably at least one primer comprises a nucleotide sequence, or complement thereof, encoding a second polypeptide, such as a Tag polypeptide, e.g., a Tag polypeptide selected from the group consisting of a myc-epitope tag and a *Haemophilus influenza* hemagglutinin protein tag.

At least one advantage of the invention relates to the fact, that no radioactive label is required. Yet another advantage of the invention is based on the fact, that relatively short polypeptides can be synthesized from the target DNA, thus providing an accurate measurement of molecular weight by mass spectrometry, compared to analysis of the DNA itself.

In one embodiment, an RNA molecule encoding a target polypeptide is translated in a cell-free extract, such as a eukaryotic cell-free extract, e.g., a reticulocyte lysate, a wheat germ extract, or a combination thereof. In another embodiment, the cell free extract is a prokaryotic cell extract, e.g., a bacterial cell extract, such as *E. coli* S30. In another embodiment, translation and transcription of a target nucleic acid are performed in a same cell-free extract, such as a reticulocyte lysate or a prokaryotic cell extract.

In a preferred embodiment of the invention a target polypeptide is isolated prior to being detected by mass spectrometric analysis. For example, the polypeptide is isolated from a cell or tissue, e.g., from a subject. The target polypeptide can be isolated using a reagent, which specifically interacts with the target polypeptide. Alternatively, the target polypeptide is fused to a Tag polypeptide and the target polypeptide is isolated using a reagent, which interacts specifically with the Tag polypeptide. A preferred reagent is an antibody. The reagent can also be a metal, e.g., nickel, with which specific Tags are capable of interacting, e.g., a hexahistidine Tag.

The invention also provides kits. In one embodiment, a kit of the invention comprises (i) a forward and a reverse primer capable of hybridizing to a nucleic acid encoding the target polypeptide and amplifying the nucleic acid; (ii) reagents necessary for in vitro transcription and translation of the amplified nucleic acid to obtain the target polypeptide; and optionally, (iii) a reagent for isolating the polypeptide; and instructions for use in determining the identity of a target polypeptide by mass spectrometric analysis. The kit can further comprise a solvent or reagent system for volatilizing the polypeptide prior to mass spectrometric analysis. In a preferred embodiment, the kit is designed for determining the number of trinucleotide repeats of a target nucleic acid. Optionally the kit further comprises a control nucleic acid and/or polypeptide of known identity.

In a preferred embodiment, the target polypeptide is encoded by an allelic variant of a polymorphic region of a gene of a subject and the process of the invention additionally comprises the steps of determining whether the allelic variant is identical to an allelic variant of the polymorphic region that is associated with a disease or condition, thereby indicating whether the subject has or is at risk of developing a disease or condition, which is associated with a specific allelic variant of the polymorphic region of the gene. The disease or condition can be associated with an aberrant number of trinucleotide repeats. Since trinucleotide repeats can be very long, determination of the number of trinucleotide repeats by analyzing the DNA would not be straightforward. However, since the invention disclosed herein is based on the analysis of a protein, preferably a polypeptide encoded essentially by the trinucleotide repeats, determination of the number of trinucleotide repeats will be more accurate using the methods and kits of the invention. The disease or condition can be Huntington's disease, prostate cancer, Fragile X syndrome type A, myotonic dystrophy type I, Kennedy disease, Machado-Joseph disease, Dentatorubral and pallidolyusian atrophy and spino bulbar muscular atrophy. Alternatively, the disease or condition can be associated with a gene selected from the group consisting of BRCA1, BRCA2, APC, dystrophin gene, $\beta$-globin, Factor IX, Factor VIIc, ornithine-d-amino-transferase, hypoxanthine guanine phosphoribosyl transferase, CFTR, and a proto-oncogene.

In another embodiment, the process and kit of the invention can be used to genotype a subject, by determining the identity of one or more allelic variants of one or more polymorphic regions in one or more genes. In a preferred embodiment, the one or more genes are associated with graft rejection and the process is for determining compatibility between a donor and recipient of a graft. For example, the gene can be a gene from the major histocompatibility complex (MHC).

In yet other embodiments of the invention, genotyping a subject according to the methods of the invention is used for forensic or identity testing purposes and the polymorphic regions are, e.g., in mitochondrial genes or are short tandem repeats (STR).

The process and kits of the invention can also be used to determine whether a subject is infected with an infectious organism, such as a virus, a bacterium, a fungi, or a protist. The invention also provides a process for determining the isotype of a specific infectious organism.

Thus, depending on the sequence to be detected, the processes and kits of the invention can be used, for example, to diagnose a genetic disease or chromosomal abnormality; a predisposition to or an early indication of a gene influenced disease or condition (e.g. obesity, artherosclerosis, diabetes, cancer), an infection by a pathogenic organism (e.g. virus, bacteria, parasite or fungus); or to provide information relating to identity (e.g., mini-and micro-satellites), heredity, or compatibility (e.g. HLA phenotyping).

Other features and advantages of the invention will be further described with reference to the following Detailed Description and claims.

BRIEF DESCRIPTION OF THE DRAWINGS

FIG. 1A (SEQ ID NO. 8) shows the nucleotide sequence of a nucleic acid that can be obtained by PCR amplification of DNA containing a non-variable stretch of 12 CAG repeats (shown without italics) and a variable repeat of 10 CAG repeat units (represented in italics) with primers having the sequence (forward primer) or the complement of the sequence (reverse primer) which is underlined. The T7 promoter sequence and sequence encoding a $(His)_6$ tail are represented in bold.

FIG. 1B (SEQ ID NO. 9) shows the amino acid sequence of a 71 amino acid polypeptide encoded by the nucleic acid sequence shown in FIG. 1A. The stretch of 10 variable glutamine residues encoded by the trinucleotide repeats is represented in italics. The $(His)_6$ tail is represented in bold.

DETAILED DESCRIPTION OF THE INVENTION

The invention provides a process for determining the identity of a target polypeptide. According to the process of the invention, a target polypeptide is obtained, e.g., from a subject, the molecular mass of the target polypeptide is determined by mass spectrometric analysis and compared to the molecular mass of a polypeptide of known identity, to thereby determine the identity of the target polypeptide. In one embodiment, the identity of a target polypeptide is the amino acid sequence of at least a portion of the target polypeptide. In a preferred embodiment, the target polypeptide is obtained by in vitro translation of an RNA molecule encoding the target polypeptide. In an even more preferred embodiment, the process further comprises in vitro transcription of a nucleic acid encoding the target polypeptide.

The invention is based at least in part on the observation that the number of CAG trinucleotide repeats and the presence of a nucleotide substitution from a C to a G in one of the trinucleotide repeats in a subject with Spino-cerebellar ataxia (SCAI) could be determined by determining the molecular mass of a polypeptide encoded by a nucleic acid comprising the trinucleotide repeats by mass spectrometry and comparing the molecular mass of the polypeptide with the molecular mass of polypeptides encoded by nucleic acids having a known number of trinucleotide repeats and known nucleotide sequence.

The identification of the nucleotide sequence of the target nucleic acid by this method was possible due to the increase in mass accuracy obtained by detecting the translation product by mass spectrometry rather than detecting the nucleic acid directly by mass spectrometry. For illustrative purpose, the open reading frame of the gene containing the $(CAG)_X$ repeat associated with Spino-cerebellar ataxia (SCAM) is illustrated in FIG. 1. As shown, it contains 10 (CAG) repeats and encodes a 7.5 kDa protein containing 10 consecutive glutamine (Q) residues. Accurate direct mass analysis of the 60 kDa 200-mer shown in FIG. 1A with currently available mass spectrometric instrumentation would be challenging. A recent study of the SCA-1 gene showed that 25–36 repeat units are typical for unaffected patients, while affected patients have 43–81 repeat units. Assuming the worst case of 81 repeat units, 213 bases in addition to the 200-mer shown in FIG. 1a, would need to be detected with sufficient resolution. However, no one has yet satisfactorily detected greater than a 400-mer (>120 kDa) by mass spectrometry. However, analysis of the translation product for the 81 repeats requires mass measurement of only about 137 amino acid residues (about 15 kDa). A typical 0.3% mass accuracy for low resolution instrumentation results in a maximum 13 Da error, far lower than the mass of a single residue. Thus, far better than single amino acid resolution is obtainable with the process of the invention.

Thus, the invention provides a fast and reliable means for indirectly obtaining nucleic acid sequence information. Since the mass of a polypeptide is only about 10% of that of the corresponding DNA, the translated polypeptide or polypeptide is typically far more amenable to mass spectrometric detection than the corresponding nucleic acid. In addition, mass spectrometric detection of polypeptides yields analytical signals of far higher sensitivity and resolution than routinely obtained with DNA, due to the latter's inherent instability to volatilization and affinity for nonvolatile cationic impurities.

Furthermore, the invention provides an efficient process for determining the presence of a single base, e.g., a single base mutation, introducing a stop codon in an open reading frame of a gene, resulting in premature protein truncation. Mutation screening by direct mass analysis of a gene, e.g., p53 or BRCA-1 genes, requires a system that permits detection of single base mutation. However, single base mutations resulting in premature stop codons may radically change the mass of the encoded protein by truncation and is thus easily identifiable according to the process of the invention.

DEFINITIONS

For convenience, the meaning of certain terms and phrases employed in the specification, examples, and appended claims are provided below.

The term "allele" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant" refers to a portion of an allele of a gene containing a polymorphic region. The term "allelic variant of a polymorphic region of a gene" refers to a region of a gene having one of several nucleotide sequences found in that region of the gene in different individuals. The term "determining the identity of an allelic variant of a polymorphic region" refers to the determination of the nucleotide sequence of a polymorphic region, thereby determining to which of the possible allelic variants of a polymorphic region that particular allelic variant corresponds.

For use in the instant invention, the "biological sample" can be any material obtained from a living source (e.g. human, animal, plant, bacteria, fungi, protist, virus). The biological sample can be in any form, including solid materials (e.g tissue, cell pellets and biopsies) and biological fluids (e.g. urine, blood, saliva, amniotic fluid and a mouth wash (containing buccal cells)).

As used herein, "determining the identity of a polypeptide" refers to determining at least one characteristic of the polypeptide, e.g., the molecular mass or charge or the identity of at least one amino acid. In preferred embodiments, determining the identity of a polypeptide is determine the amino acid sequence of at least a portion of the polypeptide.

The term "in vitro transcription system" refers to a cell-free system comprising an RNA polymerase and other factors and reagents necessary for transcription of a DNA molecule operably linked to a promoter to which the RNA polymerase specifically binds. An in vitro transcription system can also be a cell extract, e.g., eukaryotic cell extract.

The term "in vitro translation system", which is used herein interchangeably with the term "cell-free translation system" refers to a translation system which is a cell-free extract containing at least the minimum elements necessary for translation of an RNA molecule into a polypeptide. An in vitro translation system typically comprises at least ribosomes, tRNAs, initiator methionyl-tRNA$^{Met}$, proteins or complexes involved in translation, e.g., eIF$_2$, eIF$_3$, the cap-binding (CB) complex, comprising the cap-binding protein (CBP) and eukaryotic initiation factor 4F (eIF$_{4F}$).

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or polypeptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "molecular structure" of a gene or a portion thereof refers to the structure as defined by the nucleotide content (including deletions, substitutions, additions of one or more nucleotides), the nucleotide sequence, the state of methylation, and/or any other modification of the gene or portion thereof.

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous (for that gene) subject, the mutation is said to be co-dominant.

As used herein, the term "nucleic acid" refers to polynucleotides such as deoxyribonucleic acid (DNA) and ribonucleic acid (RNA) as well as analogs of either RNA or DNA, for example made from nucleotide analogs, any of which are in single or double-stranded form. As used herein, a nucleic acid can also be a portion of a longer nucleic acid molecule. For example, a nucleic acid can be a portion of a gene comprising a polymorphic region.

The term "operably linked" is intended to mean that a nucleic acid which is operably linked to a promoter is associated with the promoter in such a manner as to facilitate transcription of the nucleic acid from the promoter.

The term "polymorphism" refers to the coexistence of more than one form of a gene, i.e., allele, e.g., allelic variant or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

The terms "protein", "polypeptide" and "peptide" are used interchangeably herein when referring to a translated nucleic acid (e.g. a gene product).

The term "plasmid" refers generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "target nucleic acid" refers to any nucleic acid of interest or to a portion thereof. For example a target nucleic acid can be a polymorphic region of a gene or a region of a gene potentially having a mutation. Such "target nucleotide sequences" would include, but not be limited to, nucleotide sequence motifs or patterns specific to a particular disease and causative thereof, nucleotide sequences specific as a marker of a disease, and nucleotide sequences of interest for research purposes which may not have a direct connection to a disease. In general, "target nucleotide sequences" could be any region of contiguous nucleotides which encode a polypeptide of least 2, or preferably at least 3, at least 4, or at least 5 amino acids. A target nucleic acid encodes a target polypeptide.

The term "target polypeptide", which is used interchangeably herein with the terms "target peptide" and "target protein" refers to any polypeptide of interest which is subjected to mass spectrometry for the purposes of the invention. A target polypeptide is at least 2, preferably at least 3, at least 4, or at least 5 amino acids. Target peptides can also be longer than 5 amino acids. Target peptides can be regions of proteins which can be associated with specific diseases or conditions.

The term "transcription" as used herein, describes the process by which RNA molecules are initiated, elongated and terminated based on a DNA template. Transcription is a polymerization reaction that is catalyzed by DNA-dependent RNA polymerases. Examples of RNA polymerases for use in the instant invention include the bacterial RNA polymerases SP6 RNA polymerase, T3 RNA polymerase, and T7 RNA polymerase.

The term "translation" as used herein, describes the process by which proteins are initiated, elongated and terminated based on an RNA template. For a protein to be produced from DNA, the DNA must first be transcribed into RNA and then the RNA must be translated by the interaction of various cellular components into protein. In prokaryotic (bacterial) cells, transcription and translation are "coupled", meaning that RNA is translated into protein during the time that it is being transcribed from the DNA. In eukaryotic (e.g. plant and animal) cells, the two activities are separate, making the overall process much more complicated. DNA is transcribed into RNA inside of the cell nucleus, but the RNA is further processed into mRNA and then transported outside the nucleus to the cytoplasm where it is translated into protein.

The term "translation system" refers to a cellular or cell-free translation system. The term "cellular translation system" refers to a translation system which is a permeabilized cell, as opposed to a "cell-free translation system", which refers to a cell extract or a reconstituted translation system. The term "reconstituted translation system" refers to a system consisting of purified translation factors, such as elongation factors.

The term "wild-type allele" refers to an allele of a gene which, when present in two copies in a subject, results in a wild-type phenotype. There can be several different wild-type alleles of a specific gene, since certain nucleotide changes in a gene may not affect the phenotype of a subject having two copies of the gene with the nucleotide changes.

Isolation of a Target Polypeptide

According to the process of the invention, a target polypeptide is obtained, e.g., from a subject. In one embodiment of the invention, a polypeptide is isolated from a cell or tissue. In a preferred embodiment, a target polypeptide is synthesized in vitro from an RNA molecule. In an even more preferred embodiment, a target polypeptide is synthesized in vitro from a DNA molecule, by in vitro transcription and translation. The target polypeptide can also be synthesized in a host cell, e.g., bacterium, transformed with a DNA encoding the target polypeptide. In preferred embodiments, the polypeptide is substantially purified prior to mass spectrometric analysis. The term "substantially purified" refers to a degree of purification necessary to permit the determination of the molecular mass of the polypeptide by mass spectrometric analysis. The degree of purification necessary is known in the art and may vary according to the type of mass spectrometric analysis utilized.

In certain embodiments, the target polypeptide is a portion of a protein, which can be obtained according to methods known in the art, and involving, e.g., proteinases which cut selectively at specific amino acid sequences. Accordingly, in one embodiment of the invention a protein is obtained and the protein is subjected to limited proteolysis prior to mass spectrometric analysis.

In one embodiment, the target polypeptide is isolated from a cell, tissue or translation system, e.g., reticulocyte lysate, using a reagent, which specifically interacts with the target polypeptide. In a preferred embodiment, the reagent is an antibody, which specifically interacts with an epitope of the target polypeptide, a polypeptide encoded by trinucleotide repeats. If the target polypeptide contains an amino acid which can be any of several amino acids, e.g., in the case in which the target polypeptide can be from a mutated protein, the antibody preferably interacts with an epitope which does not include this amino acid. Antibodies can be prepared according to methods well known in the art.

In a preferred embodiment, the polypeptide is fused in frame with a Tag polypeptide, and can be obtained, e.g., by in vitro transcription and translation as described below, and the polypeptide is isolated from the translation reaction, by using a reagent which specifically interacts with the Tag polypeptide. As further set forth herein, the Tag polypeptide can be an epitope from Myc or a polypeptide from *Haemophilus influenza* hemagglutinin protein against which specific antibodies are available commercially. In a preferred embodiment, the Tag is a plurality of histidine residues, e.g., a hexahistidine, and the Tag polypeptide can thus specifically interact with zinc, nickel, or cobalt ions.

Yet in other embodiments a target polypeptide is obtained in an in vitro translation reaction from a target RNA or DNA molecule and the translation reaction is performed in the presence of a modified amino acid, by using, e.g., a misaminoacylated tRNA carrying a modified amino acid. The modification of the amino acid is chosen, so that it allows the isolation of a polypeptide comprising the modified amino acid. For example, in one embodiment, the amino acid lysine is replaced by a biotinylated lysine or other lysine analog in the translation reaction, resulting in a translated polypeptide comprising biotinylated lysine residues, which can be affinity captured on a bed of immobilized avidin or streptavidin. Other modified amino acids are disclosed in U.S. Pat. No. 5,643,722.

In a preferred embodiment, the target polypeptide is isolated by affinity purification. In one embodiment, the reagent, e.g., antibody or avidin, is linked to a solid phase surface and the translation reaction is poured over the column. In the case of a polypeptide with a $(His)_6$ tail, affinity capture can be achieved by exposure to a column or bed of chelated nickel ions. The polypeptide can then be eluted from the column, and subjected to mass spectrometry, as described below.

Mass Spectrometry

The molecular mass of the substantially pure target polypeptide is then determined by mass spectrometry.

For mass spectrometry analysis of a target polypeptide, the polypeptide is first solubilized in an appropriate solution or reagent system. The type of solution or reagent system, e.g., comprising an organic or inorganic solvent, will depend on the properties of the polypeptide and the type of mass spectrometry performed and are well known in the art (see, e.g., Vorm et al. (1994) Anal. Chem. 66:3281 (for MALDI) and Valaskovic et al. (1995) Anal. Chem. 67:3802 (for ESI). Mass spectrometry of peptides is further disclosed, e.g., in WO 93/24834 by Chait et al.

In one embodiment, the solvent is chosen so that the risk that the molecules may be decomposed by the energy introduced for the vaporization process is considerably reduced, or even fully excluded. This can be achieved by embedding the sample in a matrix, which can be an organic compound, e.g., sugar, in particular pentose or hexose, but also polysaccharides such as cellulose. These compounds are decomposed thermolytically into $CO_2$ and $H_2O$ so that no residues are formed which might lead to chemical reactions. The matrix can also be an inorganic compound, e.g., nitrate of ammonium which is decomposed practically without leaving any residues. Use of these and other solvents are further disclosed in U.S. Pat. No. 5,062,935 by Schlag et al.

Preferred mass spectrometer formats for use in analyzing the translation products include ionization (I) techniques, including but not limited to matrix assisted laser desorption (MALDI), continuous or pulsed electrospray (ESI) and related methods (e.g., Ionspray or Thermospray), or massive cluster impact (MCI); these ion sources can be matched with detection formats including linear or non-linear reflectron time-of-flight (TOF), single or multiple quadrupole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected, for example, using ESI (Valaskovic, G. A. et al., (1996) Science 273:1199–1202) or MALDI (Li, L. et al., (1996) J. Am. Chem. Soc. 118:1662–1663) mass spectrometry.

ES mass spectrometry has been introduced by Fenn et al. (J. Phys. Chem. 88, 4451–59 (1984); PCT Application No. WO 90/14148) and current applications are summarized in recent review articles (R. D. Smith et al., Anal. Chem. 62, 882–89 (1990) and B. Ardrey, Electrospray Mass Spectrometry, Spectroscopy Europe, 4, 10–18 (1992)). MALDI-TOF mass spectrometry has been introduced by Hillenkamp et al. ("Matrix Assisted UV-Laser Desorption/Ionization: A New Approach to Mass Spectrometry of Large Biomolecules," Biological Mass Spectrometry (Burlingame and McCloskey, editors), Elsevier Science Publishers, Amsterdam, pp. 49–60, 1990). With ESI, the determination of molecular weights in femtomole amounts of sample is very accurate due to the presence of multiple ion peaks which all could be used for the mass calculation.

The mass of the target polypeptide determined by mass spectrometry is then compared to the mass of a reference polypeptide of known identity. In one embodiment, the target polypeptide is a polypeptide containing a number of repeated amino acids directly correlated to the number of trinucleotide repeats transcribed/translated from DNA; from its mass alone the number of repeated trinucleotide repeats in the original DNA which coded it, may be deduced.

Isolation of Nucleic Acids

According a preferred embodiment of the invention, a target polypeptide is obtained from an RNA molecule, preferably by in vitro translation of the RNA molecule. In an even more preferred embodiment, the target polypeptide is obtained from a DNA molecule, and further comprises a step of in vitro transcribing at least a portion of the DNA molecule. In a preferred embodiment, at least a portion of the DNA molecule, comprising the nucleotide sequence encoding the target polypeptide is first amplified, e.g., by PCR, as further described herein. Thus, in a preferred embodiment, the process of the invention comprises obtaining a nucleic acid molecule, either DNA or RNA, from which the target polypeptide is obtained.

According to the process of the invention, any nucleic acid, in purified or non purified form, can be utilized as the starting nucleic acid or acids, provided it is suspected of containing the target nucleic acid. As used herein, the term "starting nucleic acid" refers to a at least one molecule of a nucleic acid comprising a target nucleic acid, i.e., nucleic acid encoding a target polypeptide. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from an amplification. The target nucleic acid may be only a fraction of a larger molecule or can be present initially as a discrete molecule, so that the specific sequence constitutes the entire nucleic acid.

It is not necessary that the target nucleic acid be present initially in a pure form; it may be a minor fraction of a complex mixture, such as a portion of the β-globin gene contained in whole human DNA, or a portion of nucleic acid sequence of a particular microorganism which organism might constitute only a very minor fraction of a particular biological sample. The starting nucleic acid may contain more than one target nucleic acid which may be the same or different.

The starting nucleic acid or acids may be obtained from any source, for example, from plasmids such as pBR322, from cloned DNA or RNA, or from natural DNA or RNA from any source, including bacteria, yeast, viruses, organelles, and higher organisms such as plants or animals.

In a preferred embodiment of the invention, the starting nucleic acid represents a sample of DNA isolated from an animal or human patient. This DNA may be obtained from any cell source or body fluid. Non-limiting examples of cell sources available in clinical practice include blood cells, buccal cells, cervicovaginal cells, epithelial cells from urine, or any cells present in tissue obtained by biopsy. Body fluids include blood, urine, cerebrospinal fluid, and tissue exudates at the site of infection or inflammation.

DNA is extracted from the cell source or body fluid using any of the numerous methods that are standard in the art. It will be understood that the particular method used to extract DNA will be chosen as being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction and/or phenol extractions can be used to obtain nucleic acid from cells or tissues, e.g., blood (Rolff, A et al. PCR: Clinical Diagnostics and Research, Springer (1994)).

In a specific embodiment, the cells may be directly used without purification of the target nucleic acid. For example, the cells can be suspended in hypotonic buffer and heated to about 90°–100° C., until cell lysis and dispersion of intracellular components occur, generally about 1 to 15 minutes. After the heating step the amplification reagents may be added directly to the lysed cells. This direct amplification method may be used on peripheral blood lymphocytes and amniocytes.

The preferred amount of DNA to be extracted for analysis of human genomic DNA is at least 5 pg (corresponding to about 1 cell equivalent of a genome size of $4 \times 10^9$ base pairs). In some applications, such as, for example, detection of sequence alterations in the genome of a microorganism, variable amounts of DNA may be extracted.

In one embodiment, the starting nucleic acid is RNA obtained, e.g., from a cell or tissue. RNA can be obtained from a cell or tissue according to various methods known in the art and described, e.g., in Molecular Cloning A Laboratory Manual, 2nd Ed., ed. by Sambrook, Fritsch and Maniatis (Cold Spring Harbor Laboratory Press: 1989).

Amplification of the Target Nucleic Acid Sequence

In a preferred embodiment, the process of the invention further comprises amplifying at least a portion of a target nucleic acid prior to obtaining the polypeptide encoded by the target nucleic acid, e.g., prior to in vitro transcription and translation of the target nucleic acid.

The term "amplifying" refers to the repeated copying of sequences of deoxyribonucleic acids (DNA) or ribonucleic acids (RNA) through the use of specific or non-specific means resulting in an increase in the amount of the specific DNA or RNA sequences intended to be copied. These processes include the Polymerase Chain Reaction (PCR)(C. R. Newton and A. Graham, PCR, BIOS Publishers, 1994), Nucleic Acid Sequence Based Amplification (NASBA), Transcription-based Amplification System (TAS), Self-sustained Sequence Replication (SSR), Q-beta replicase, Ligation Amplification Reaction (LAR), Ligase Chain Reaction (LCR) (Wiedmann, M., et. al., (1994) PCR Methods Appl. Vol. 3, Pp. 57–64; F. Barany *Proc. Natl. Acad. Sci USA* 88, 189–93 (1991)), strand displacement amplification (SDA) (G. Terrance Walker et al., *Nucleic Acids Res.* 22, 2670–77 (1994)), and variations such as RT-PCR (Higuchi, et al., *Bio/Technology* 11:1026–1030 (1993)), allele-specific amplification (ASA).

In a preferred embodiment, a nucleotide sequence of the target nucleic acid is amplified by PCR. Reactions conditions for PCR are well known in the art and usually include at least a template DNA molecule, a forward and a reverse primer, both of which are capable of hybridizing to the template DNA molecule, four different nucleoside triphosphates, an agent for polymerization such as DNA polymerase, and an appropriate buffer ("buffer" includes pH, ionic strength, cofactors, etc.). Typically about 25–30 amplification cycles (comprising a denaturation step, an annealing step and an extension step) are performed, but fewer cycles may be sufficient or more cycles may be required, depending, e.g., on the amount of the template DNA molecules present in the reaction. Examples of PCR reaction conditions can be found, e.g., in U.S. Pat. No. 5,604,099, issued to Hoffmann-LaRoche, Inc., Nutley, N.J.

In one embodiment, a nucleic acid sequence is amplified using the polymerase chain reaction disclosed in U.S. Pat. No. 5,545,539, assigned to Genzyme Corporation, Cambridge, Mass. The method of amplification disclosed in this patent is an improvement of the procedure for amplifying a target nucleotide sequence, by using an effective amount of a glycine-based osmolyte in the reaction mixture of the amplification procedure. It has been found that the use of a glycine-based osmolyte improves amplification of sequences rich in Gs and Cs, e.g., amplification of trinucleotide repeat sequence, such as those characteristic of Fragile X Syndrome (CGG repeats) or myotonic dystrophy (CTG repeats).

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced. Preferred primers for use according to the invention are capable of hybridizing specifically to sequences which are adjacent to the sequence of interest, i.e., target sequence. Alternatively, the primers can hybridize to the target sequence.

Any specific nucleic acid sequence can be amplified by PCR. It is only necessary that a sufficient number of bases at the ends of the target sequence or in the target sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process.

The primer must be sufficiently long to prime the synthesis of extension products in the presence of the agent for polymerization. The exact lengths of the primers will depend on many factors, including temperature and source of primer and use of the method. For example, depending on the complexity of the target sequence, the oligonucleotide primer typically contains 15–25 nucleotides, although it may contain more or fewer nucleotides. Short primer molecules generally require lower temperatures to form sufficiently stable hybrid complexes with the template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. However, it is preferred that the primers have exact complementarity with a sequence from the target nucleic acid or complement thereof to obtain the best amplification.

It will be understood that the word "primer" as used hereinafter may refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be homologous with the end of the desired sequence to be amplified.

In a preferred embodiment, the forward and/or the reverse primer comprises a nucleotide sequence of a promoter, such as a bacteriophage promoter, e.g., SP6, T3 or T7 promoter. Amplification of a nucleotide sequence using such primers will result in an amplified DNA operably linked to a promoter, which can then be used in an in vitro transcription reaction to transcribe the amplified, target, nucleic acid sequence. The nucleotide sequences of the SP6, T3, and T7 promoter are set forth below:

```
SP6 promoter sequences:
5'd(CATACGATTTAGGTGACACTATAG)3'    SEQ ID NO. 1;

5'd(ATTTAGGTGACACTATAG)3'          SEQ ID NO. 2;

T3 promoter sequence:
5'd(ATTAACCCTCACTAAAGGGA)3'        SEQ ID NO. 3; and

T7 promoter sequence:
5'd(TAATACGACTCACTATAGGG)3'        SEQ ID NO. 4.
```

In a preferred embodiment of the invention, the primer comprising a promoter further comprises an initiation (ATG) codon located downstream of the promoter, such that amplification of the target nucleic acid results in an amplified target sequence comprising an ATG codon in frame with the desired reading frame. The reading frame can be the natural reading frame or can be any other reading frame. In certain embodiments, the target polypeptide does not exist naturally and the nucleic acid encoding the target polypeptide will be linked to an artificial initiation codon initiating translation in the desired reading frame.

In another preferred embodiment of the invention, the forward and/or reverse primer comprise a nucleotide sequence, or the complement of a nucleotide sequence (if present in the reverse primer), encoding a second polypeptide. The second polypeptide can be a Tag, i.e., a polypeptide, against which reagents, e.g., antibodies, interacting specifically with the Tag polypeptide are available or can be prepared. The fusion of such Tag peptides to peptides of interest allow the detection and isolation of the polypeptide of interest. Thus, a polypeptide encoded by the target nucleic acid fused to a Tag polypeptide can be isolated from the in vitro translation reaction mixture, by using a reagent interacting specifically with the Tag polypeptide, prior to subjecting the polypeptide to mass spectrometry.

Numerous Tag peptides are available commercially. However, any polypeptide can be used as a Tag so long as a reagent, e.g., an antibody interacting specifically with the Tag polypeptide is available or can be prepared or identified. Frequently used Tag include myc-epitopes (e.g., see Ellison et al. (1991) *J Biol Chem* 266:21150–21157) which includes a 10-residue sequence from c-myc, the pFLAG system (international Biotechnologies, Inc.), the pEZZ-protein A system (Pharmacia, N.J.), a 16 amino acid portion of the *Haemophilus influenza* hemagglutinin protein, or a hexahistidine. The reagents interacting specifically with the Tag polypeptide can be antibodies. However, the reagents can also be any molecule, e.g., nickel ions, with which, e.g., a hexahistidine is capable of interacting.

Alternatively, the second polypeptide can be designed to, in addition, serve as a mass modifier of the polypeptide encoded by the target nucleic acid. Modification of the mass of the polypeptide derived from the target nucleic acid is useful, e.g., in situations in which several peptides are analyzed in a single mass spectrometric analysis.

In fact, in one embodiment of the invention, more than one target nucleic acid is amplified in the same reaction. Thus, e.g., several pairs of primers can be contacted with a starting nucleic acid for amplifying different target nucleic acid sequences. Amplification can be performed simultaneously so long as the annealing temperature of all the primer pairs is sufficiently close. Alternatively, amplification can be performed with a first pair of primers having the lower annealing temperature of the several pairs of primers, and then adding the second pair of primers and performing the second amplification at the higher annealing temperature. Reaction with different primer pairs can also be performed in different reactions and then pooled. Accordingly, the instant invention is also useful for simultaneously determining the identity of more than one allelic variant of one or more polymorphic regions of one or more genes, and/or genetic lesion.

In another embodiment of the invention, a primer, preferably the forward primer comprises regulatory sequence elements necessary for translation of an RNA in a prokaryotic system. In fact, in certain embodiments, it is desirable to perform a translation reaction in a prokaryotic translation system, as described below. Accordingly, in a preferred embodiment, a primer comprises a prokaryotic ribosome binding sequence (Shine-Dalgarno sequence), located downstream of a promoter sequence and about 5–10 nucleotides upstream of the initiation codon. In one embodiment, the prokaryotic ribosome binding sequence has the nucleotide sequence: TAAGGAGG (SEQ ID NO. 5).

In another preferred embodiment, a primer, preferably the reverse primer, contains a STOP codon in one or more of the reading frames to assure proper termination of the polypeptide. Further, by incorporating into the reverse primer three stop codons in the three possible reading frames, optionally separated by several residues, additional mutations that occur after a mutation that results in premature termination, can be detected.

For preparing the primers for the amplification process, the nucleotide sequences of numerous target genes can be obtained from GenBank (publicly available on the internet at http://www.ncbi.nlm.nih.gov), in relevant journal articles, patents and/or patent applications. The oligonucleotide primers may be prepared using any suitable method, such as, for example, the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared that can then be joined together to form longer nucleic acids. For a description of this method, see Narang, S. A., et al., Meth. Enzymol., 68, 90 (1979) and U.S. Pat. No. 4,356,270. Primers can also be synthesized as disclosed in any of U.S. Pat. Nos. 5,547,835; 5,605,798; and 5,622,824 by Köster.

In one embodiment of the invention, the primers for the amplification are selected such that the amplification results in a nucleic acid which upon transcription and translation results in a non-naturally occuring polypeptide. In one embodiment, the polypeptide is encoded by an open reading frame which is not the open reading frame encoding the natural polypeptide. Accordingly, by appropriate primer design (in particular, by including an initiation codon downstream of a promoter in one of the primers), the polypeptide produced from the target nucleic acid is encoded by any of the two non-coding frames of the nucleic acid. This can be used to shift out of frame stop codons which prematurely truncate the protein and exclude relevant amino acids, or to make the polypeptide containing the amino acid repeat more soluble.

The non-naturally occuring polypeptide can also be encoded by a 5' or 3' non coding region of an exonic region of a nucleic acid, by an intron, or by a promoter sequence which contains in one of the six frames (3 frames per strand) at least a portion of an open reading frame. In these situations, one primer for amplification of the target nucleic acid comprises a promoter and an initiation codon, such that the amplified nucleic acid can be in vitro transcribed and translated. Thus, the method of the invention permits the determination of the identity of a nucleotide sequence located in any region of a gene, so long as a polypeptide of at least 2, preferably 3, 4, or 5 amino acids is encoded by any one of the six frames.

Transcription and Translation of a Target Nucleic Acid

In a preferred embodiment of the invention, the target polypeptide is obtained from in vitro translation of a RNA molecule encoding a target polypeptide. In an even more preferred embodiment, the RNA molecule is obtained from in vitro transcription of a DNA molecule encoding the target polypeptide.

To allow in vitro transcription, the target DNA is preferably operably linked to a promoter from which transcription is initiated in the presence of an RNA polymerase capable of interacting with the promoter, ribonucleotides, and other reagents necessary for in vitro transcription. In vitro transcription can be performed as a separate step from the in vitro translation. Alternatively, transcription and translation can be carried out in a same reaction.

An in vitro transcription reaction can be carried out according to methods well known in the art, and described, e.g., in Molecular Cloning A Laboratory Manual, 2nd Ed., ed. by Sambrook, Fritsch and Maniatis (Cold Spring Harbor Laboratory Press: 1989) and in U.S. Pat. No. 4,766,072, assigned to Promega Corp., disclosing vectors for in vitro transcription. In vitro transcription kits are also commercially available from several manufacturers, e.g., Promega Corp.

In a preferred embodiment, an in vitro transcription reaction is carried out as follows. The template DNA, i.e., target nucleic acid, is incubated for about 1 hour at 37° C. or 40° C. (depending on the polymerase) in the presence of ribonucleotides, a cap analog (GpppG or a methylated derivative thereof), an RNAase inhibitor, an RNA polymerase recognizing the promoter that is operably linked upstream of the DNA to be transcribed, and an appropriate buffer containing Tris.Cl, $MgCl_2$ spermidine and NaCl. Following the transcription reaction, RNAase free DNAse can be added to remove the DNA template and the RNA purified by, e.g., a phenol-chloroform extraction. Usually about 5–10 µg of RNA can be obtained per microgram of template DNA. Further details regarding this protocol are set forth, e.g., in Molecular Cloning A Laboratory Manual, 2nd Ed., ed. by Sambrook, Fritsch and Maniatis (Cold Spring Harbor Laboratory Press: 1989).

RNA can also be produced in a non-capped form, such as by in vitro transcription in the absence of a cap analog. In fact, translation of an RNA in a prokaryotic system does not require the presence of an $N_7$-methyl-G (a "CAP") covalently linked to the 5' end of the mRNA. However, since capped RNA is translated much more efficiently than uncapped RNA in eukaryotic systems, it is preferable to cap the RNA during transcription or alternatively, during translation, when using a eukaryotic translation system.

In one embodiment, the RNA is then isolated, e.g., by ethanol precipitation, and the RNA is subjected to in vitro translation, e.g., as set forth below.

Translation systems may be cellular or cell-free, and may be prokaryotic or eukaryotic. Cellular translation systems, as used herein, refer to cells or permeabilized cells. Cell-free translation systems, as used herein, refer to cell or tissue extracts, and are also referred to herein as "in vitro translation systems".

In a preferred embodiment, the translation system is an in vitro translation system. In vitro translation systems are commercially available and many different types and systems are well known. Examples of in vitro translation systems include eukaryotic lysates, such as rabbit reticulocyte lysates, rabbit oocyte lysates, human cell lysates, insect cell lysates and wheat germ extracts. Extracts are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes.

Mixtures of purified translation factors, as well as combinations of lysates or lysates supplemented with purified translation factors such as initiation factor-1 (IF-1), IF-2, IF-3 (alpha or beta), elongation factor T (EF-Tu) or termination factors can also be used to obtain mRNA translation.

Incubation times range from about 5 minutes to many hours, but is preferably between about thirty minutes to about five hours and more preferably between about one to about three hours. Incubation may also be performed in a continuous manner whereby reagents are flowed into the system and nascent proteins removed or left to accumulate using a continuous flow system (A. S. Spirin et al., Sci. 242:1162–64, 1988). This process may be desirable for large scale production of nascent proteins. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C. and even more preferably at about 25° C. or about 37° C.

Translation mixes will typically comprise buffers such as Tris-HCl, Hepes or another suitable buffering agent to maintain the pH of the solution between about 6 to 8, and preferably at about 7. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process. Preferred translation systems and translation conditions are further described below.

In a preferred embodiment, the in vitro translation system is a reticulocyte lysate, which is available commercially or can be prepared according to methods known in the art and briefly outlined below. Commercially available reticulocyte lysates are available from, e.g., New England Nuclear and Promega Corp. (Cat. # L4960, L4970, and L4980). In another embodiment, the in vitro translation system is a wheat germ translation system. Such a system is also available commercially or can be prepared according to methods known in the art. Commercially available wheat germ extracts can be obtained, e.g., from Promega Corp. (e.g., Cat # L4370). In yet another preferred embodiment, the in vitro translation system is a mixture of a reticulocyte lysate and a wheat germ extract. Such a mixture can be obtained commercially, e.g., from Promega Corp. (e.g., Cat.# L4340). Other in vitro translation systems that can be used according to the method of the invention include *Escherichia coli* extracts, insect cell extracts and frog oocytes extracts.

One embodiment uses reticulocyte lysates. A rabbit reticulocyte lysate can be prepared as follows. Rabbits are rendered anemic by inoculation with acetylphenylhydrazine. About 7 days later, the rabbits are bled and the blood is collected and mixed with an ice cold salt solution containing NaCl, Mg acetate, KCl, and heparin. The blood is then filtered through a cheesecloth, centrifuged, and the buffy coat of white cells is removed. The pellet consisting of erythrocytes and reticulocytes is then washed with the salt solution, prior to being lyzed by the addition of an equal volume of cold water. Endogenous RNAs are degraded by treating the lysate with micrococcal nuclease and calcium ions (necessary for the activity of the enzyme) and the reaction stopped by the addition of EGTA, which chelates the $CaCl_2$ and thereby inactivate the nuclease. Hemin is usually added to the lysate (at a concentration of about 20–80 $\mu$M), since it is a powerful suppressor of an inhibitor of the initiation factor eIF-2. The lysates can further be optimized by the addition of an energy generating system, consisting of phosphocreatine kinase and phosphocreatine. The lysates can then be aliquoted and stored at −70° C. or in liquid nitrogen. Further details regarding this protocol are set forth, e.g., in Molecular Cloning A Laboratory Manual, 2nd Ed., ed. by Sambrook, Fritsch and Maniatis (Cold Spring Harbor Laboratory Press: 1989).

An in vitro translation reaction using a reticulocyte lysate can be carried out as follows. Ten $\mu$l of a reticulocyte lysate, e.g., prepared as set forth above or a commercial lysate, is mixed with spermidine, creatine phosphate, amino acids, HEPES buffer (pH 7.4), KCl, magnesium acetate and RNA to be translated and incubated for an appropriate time, e.g., one hour, at 30° C. The optimum amount of magnesium acetate for obtaining efficient translation will vary from one reticulocyte lysate to another, and can be determined using a standard preparation of RNA and concentration of magnesium acetate varying from 0–1 mM. The optimal concentration of KCl can also be different depending on the specific reaction. For example, 70 mM KCl is usually optimal for translation of capped RNAs and 40 mM is usually optimal for translation of uncapped RNAs. Optionally, the translation process is monitored, such as by mass spectrometric analysis. Alternatively, monitoring can be performed, e.g., by adding one or more amino acids as radioactive amino acids, e.g., $^{35}$S methionine (further described below). In this case, the translation process can be monitored by precipitating the proteins in the lysate, e.g., TCA precipitating and counting the amount of radioactivity present in the precipitate. The translation products can also be analyzed by immunoprecipitation and/or SDS-polyacrylamide gel electrophoresis. Further details regarding this protocol are set forth, e.g., in Molecular Cloning A Laboratory Manual, 2nd Ed., ed. by Sambrook, Fritsch and Maniatis (Cold Spring Harbor Laboratory Press: 1989).

Another preferred embodiment utilizes wheat germ extract. A wheat germ extract can be prepared by a method described by Roberts, B. E. and Paterson, B. M. (1973), Proc. Natl. Acad. Sci. USA Vol. 70, No. 8, pp. 2330–2334), and can further be modified according to Anderson, C. W., et al. (1983, Meth. Enzymol. Vol.101, p. 635). The protocol can further be modified according to the manufacturing protocol L418, Promega Corp. Madison, Wis. Generally, wheat germ extract is prepared by grinding wheat germ in an extraction buffer, followed by centrifugation to remove cell debris. The supernatant is then separated by chromatography from endogenous amino acids and plant pigments that are inhibitory to translation. The extract is also treated with micrococcal nuclease to destroy endogenous mRNA, to reduce background translation to a minimum. The extract contains the cellular components necessary for protein synthesis, such as tRNA, rRNA and initiation, elongation, and termination factors. The extract can further be optimized by the addition of an energy generating system consisting of phosphocreatine kinase and phosphocreatine, and magnesium acetate is added at a level recommended for the translation of most mRNA species. The final magnesium concentration for standard wheat germ extract, is typically in the range of about 6.0 to 7.5 mM.

Translations in wheat germ extracts can be performed as described, e.g., in Erickson and Blobel (1983) Methods Enymol. 96:38. This protocol can also be modified, e.g., by adjusting the final ion concentrations at 2.6 mM magnesium and 140 mM potassium and the pH at 7.5 (as described in U.S. Pat. No. 4,983,521). In a preferred embodiment, reaction mixtures are incubated at 24° C. for 60 minutes. Translations in wheat germ extracts can also be performed according to the protocol set forth in U.S. Pat. No. 5,492,817.

Translation reactions can be optimized by the addition of ions and/or other reagents. For example, magnesium is known to be important for optimizing translation, as it enhances the stability of assembled ribosomes and functions in their binding together during translation. Magnesium also appears to play a role in facilitating polymerase binding. Potassium is important as well for optimizing translation, but unlike the case for magnesium, for coupled transcription and translation the concentration of potassium ions does not need to be altered beyond standard translation preparation levels.

Potassium and magnesium are in the standard rabbit lysate. The levels are partially from the endogenous lysate levels, and partially from the additions made in the preparation of the lysate, as are done for translation lysates.

As the magnesium concentration should be adjusted to within a rather narrow optimal range for optimal translation, it is preferred that the lysate magnesium levels be measured directly through the use of a magnesium assay, prior to the addition of extra magnesium, so that the amount of magnesium in a reaction can be standardized from one batch of lysate to the next. The Lancer "Magnesium Rapid Stat Diagnostic Kit" (Oxford Lab Ware Division, Sherwood Medical Co., St. Louis, Mo.), is one such assay which can accurately measure the magnesium levels in biological fluid. Once the magnesium ion concentration for a given batch of lysate is known then additional magnesium, for instance in the form of a concentrated magnesium salt solution, can be added in a known manner to bring the magnesium concentration of the lysate to within the optimal range, or, in the case of a modified lysate preparation to be used as one-half of a reaction mixture, to within twice the optimal range.

In a preferred embodiment of the invention, the final magnesium concentration of rabbit reticulocyte lysate is adjusted, such as by adding a concentrated solution of magnesium chloride or acetate, to a concentration greater than 2.5 mM but less than 3.5 mM, preferably between 2.6 mM and 3.0 mM.

One common addition to translation reactions is an amount of a polyamine sufficient to stimulate the efficiency of chain elongation. Accordingly, spermidine can be added to a reticulocyte lysate translation reaction to a final concentration of about 0.2 mM. Spermidine is also preferably added to wheat germ extracts, preferably at a concentration of about 0.9 mM. Since the presence of polyamines are known to lower the effective magnesium concentration for translation reactions, the presence of spermidine in translation reactions should be taken into consideration when determining the appropriate concentration of magnesium to use.

In another embodiment, dithiothreitol (DTT) is added to the translation mixture. DTT is preferably added to a final concentration of about 1.45 mM in reticulocyte lysates and at 5.1 mM in wheat germ extracts.

Translation systems can also be supplemented with certain factors, e.g., tRNA molecules. Such molecules are commercially available, e.g., from a number of sources and can be prepared using well-known methods from sources including *Escherichia coli*, yeast, calf liver and wheat germ cells (Sigma Chemical, St. Louis, Mo.; Promega Corp., Madison, Wis.; Boehringer Mannheim Biochemicals, Indianapolis, Ind.). Their isolation and purification mainly involves cell-lysis, phenol extraction followed by chromatography on DEAE-cellulose. Amino-acid specific TRNA, for example tRNA<fMet>, can be isolated by expression from cloned genes and overexpressed in host cells and separated from total tRNA by techniques such as preparative polyacrylamide gel electrophoresis followed by band excision and elution in high yield and purity (Seong and RajBhandary, Proc. Natl. Acad. Sci. USA 84:334–338, 1987).

Translation efficiency can also be improved, e.g., by adding RNAase inhibitors, e.g., RNasin® or heparin to the translation reaction. RNasin® can be obtained, e.g., from Promega Corp. (e.g., Cat # N2514). In a preferred embodiment about 40 units of RNasin® are added to a 50 $\mu$l reaction. Although the addition of RNAase inhibitors in reticulocyte lysates is not crucial, only limited translation occurs if no RNAase inhibitor is added to a translation reaction using a wheat germ extract.

In a preferred embodiment, the translation process, including the movement of the ribosomes on the RNA molecules, is inhibited at an appropriate time by the addition of an inhibitor or translation, e.g., cycloheximide. Accordingly, in one embodiment, cycloheximide is added at a final concentration of 1 $\mu$g/ml to the translation reaction. $Mg^{2+}$, e.g., $MgCl_2$, e.g., at a concentration of 5 mM can also be added to maintain the mRNA-80s ribosome-nascent polypeptide complexes (polysomes).

For determining the optimal in vitro translation conditions, translation of mRNA in an in vitro system can optionally be followed, e.g., by mass spectrometric analysis. Alternatively, a labeled amino acid can be included in the translation reaction together with an amino acid mixture depleted in this specific amino acid. A preferred labeled amino acid is a radioactively labeled amino acid, e.g., $^{35}S$ methionine. Alternatively, a labeled non-radioactive amino acid can be incorporated into the nascent polypeptide. For example, the translation reaction can comprise a misaminoacylated tRNA, as described in U.S. Pat. No. 5,643,722. Accordingly, a non-radioactive marker, is misaminoacylated to a tRNA molecule and this tRNA is added to the translation system. The system is incubated to incorporate the marker into the nascent polypeptide and polypeptides containing the marker can be detected using a detection method appropriate for the specific marker. The translation process can also be followed by spectrometric analysis, and does not therefore require the use of radioactivity or other label.

In another embodiment, misaminoacylation of a tRNA molecule is used to add a marker to the polypeptide for facilitating the purification of the polypeptide. As set forth above, such markers, e.g., biotin, streptavidin and derivatives thereof are further described in U.S. Pat. No. 5,643,722.

In another embodiment of the invention in which the RNA is transcribed in vitro from template DNA, the in vitro transcription and translation reactions are performed simultaneously. This can be done, e.g., by using commercially available systems, such as the Coupled Transcription/Translation System of Promega Corp. (Cat # L4600, 4610, and 4950). Coupled transcription and translation systems using RNA polymerases and eukaryotic lysates are further described in U.S. Pat. No. 5,324,637.

Coupled in vitro transcription and translation can also be carried out using a prokaryotic system, such as a bacterial system, e.g., *E. coli* S30 cell-free extracts. Such extracts are described, e.g., by Zubay, G. (1973) *Ann Rev Genet* 7:267. Although such prokaryotic systems allow coupled in vitro transcription and translation, they may also be used for in vitro translation only. When using a prokaryotic translation system, it is preferable that the RNA comprise sequence elements necessary for translation of an RNA in a prokaryotic system. For example, it is preferable that the RNA contain prokaryotic ribosome binding sites. Accordingly, in a preferred embodiment, a target nucleic acid sequence is amplified using a primer containing a prokaryotic ribosome binding sequence, as described above. The nbosome binding sequence is preferably located downstream of a promoter for use in in vitro transcription.

Cell-based translation systems can be prepared as follows. Cells can be permeabilized by incubation for a short period of time in a solution containing low concentrations of detergents in a hypotonic media. Useful detergents include Nonidet-P 40 (NP40), Triton X-100 (TX-100) or deoxycholate at concentrations of about 0.01 nM to 1.0 mM, preferably between about 0.1 mu M to about 0.01 mM, and more preferably about 1 $\mu$M. Such systems can be formed from intact cells in culture such as bacterial cells, primary cells, immortalized cell lines, human cells or mixed cell populations.

In yet another embodiment of the invention, the target polypeptide is obtained from a host cell transformed with, and expressing, a nucleic acid encoding the target polypeptide. Accordingly, the target nucleic acid can be amplified, e.g., by PCR, inserted into an expression vector, and the expression vector introduced into a host cell in which the polypeptide encoded by the target nucleic acid can be expressed. Host cells can be eukaryotic or prokaryotic. Preferred eukaryotic host cells include mammalian cells, e.g., human host cells. Preferred prokaryotic cells include bacteria, e.g., *E. coli*. Eukaryotic and prokaryotic expression vectors are well known in the art and can be obtained commercially. Following expression in the host cell, the target polypeptide can then be isolated using methods, such as those described herein. For example, if the target polypeptide comprises a hexahistidine tail, the target polypeptide can be purified by affinity chromatography on a chelated nickel column.

Exemplary Uses

The invention provides methods for determining the identity of a target polypeptide. Knowing the identity of the target polypeptide can then be used, in certain embodiments of the invention, to obtain information on the DNA sequence encoding the target polypeptide. The target polypeptide can be from a eukaryote, such as a vertebrate, e.g., a mammal. A preferred mammal is a human. The target polypeptide can also be from a prokaryote, e.g., a bacterium or from a virus. Generally, the target polypeptide can be from any organism or plant.

Depending on the target polypeptide to be detected, the process of the invention can be used, for example, to diagnose a genetic disease or chromosomal abnormality; a predisposition to or an early indication of a gene influenced disease or condition (e.g. obesity, artherosclerosis, diabetes, cancer), an infection by a pathogenic organism (e.g. virus, bacteria, parasite or fungus); or to provide information relating to identity (e.g., mini-and micro-satellites), heredity, or compatibility (e.g. HLA phenotyping).

In a preferred embodiment, the invention provides a method for detecting specific types of genetic lesions, which are characterized by an abnormal number of trinucleotide repeats, which can range from less than 10 to more than 100 additional trinucleotide repeats, relative to the gene in a non-affected individual. These diseases include: Huntington's disease, prostate cancer, Spinal Cerebellar Ataxia (SCA), Fragile X syndrome (Kremer et al., Science 252:1711–14 (1991); Fu et al., Cell 67:1047–58 (1991); Hirst et al. J. Med. Genet. 28:824–29 (1991)), Myotonic Dystrophy (MD) type I ( Mahadevan et al., Science 255:1253–55 (1992); Brook et al., Cell 68:799–808 (1992)), Kennedy's disease, also termed Spinal and Bulbar Muscular Atrophy (La Spada et al., Nature 352:77–79 (1991)), Machado-Joseph disease, Dentatorubral and Pallidolyusian Atrophy. The aberrant number of triplet repeats can be located in any region of a gene, including the coding regions, non-coding regions of exons, introns, and promoter. For example, the expanded trinucleotide repeat associated with myotonic dystrophy occurs in the 3' untranslated region (UTR) of the MtPK gene on chromosome 19. In some of these diseases, e.g., prostate cancer, the number of trinucleotide repeats is positively correlated with prognosis of the disease. Thus, a higher number of trinucleotide repeats correlates with a poorer prognosis.

In another embodiment, the invention provides, more generally, a process for determining the identity of the allelic variant of a polymorphic region of a gene, e.g., a human gene. The allelic variants can differ in the identity of a single nucleotide or base pair (i.e., by substitution of one nucleotide), in two or more nucleotides or base pairs, or in the number of nucleotides (i.e., additions or deletions of nucleotides, e.g., or addition of trinucleotide repeats), or chromosomal rearrangements (e.g., translocations). Specific allelic variants of polymorphic regions are associated with specific diseases and in some cases correlate with the prognosis of the disease. A specific allelic variant of a polymorphic region associated with a disease is referred to herein as a "mutant allelic variant", and is said to have a "genetic lesion".

Thus, the method of the invention can be used to determine the genetic nature of a phenotype, or to recognize a predisposition to that phenotype. In particular, the method of the invention can be used to determine whether a subject has a predisposition to a specific disease or condition, i.e., whether a subject has or is at risk of developing a disease or condition associated with a specific allelic variant of a polymorphic region of a gene, comprising determining whether the subject carries an allelic variant associated with the specific disease or condition. Alternatively, if the disease is a recessive disease, the method of the invention can be used to determine whether a subject carries an allele of a gene which is associated with a specific disease or condition.

Numerous diseases or conditions have been genetically linked to a specific gene, or more particularly with a specific mutation or genetic lesion of a gene. For example, hyperproliferative diseases, e.g., cancers, have been associated with mutations in specific genes. Such cancers include breast cancer, which has been linked to mutations in BRCA1 and/or BRCA2. Mutant alleles of BRCA1 are disclosed, e.g., in U.S. Pat. No. 5,622,829. Other genes, in particular tumor suppressor genes, which mutated, can cause or contribute to the development of cancer include: p53 (resulting in many forms of cancer); Rb gene (resulting in retinoblastoma); WT1 (resulting in Wilm's tumor); and various proto-oncogenes, e.g., c-myc and c-fos. Numerous other genes associated with specific diseases are disclosed in medical textbooks, e.g., Thompson and Thompson, Genetics in Medicine, 5th Ed., and Nora et al., Medical Genetics, fourth Ed. Lea & Febiger Eds.

In a preferred embodiment, the process of the invention is used to detect DNA mutations which eventually translate into a truncated polypeptide, as is commonly the case with BRCA1 and BRCA2. In fact, translation of nucleic acid regions comprising such a mutation will result in a truncated polypeptide, which can easily be differentiated from the non truncated polypeptide by mass spectrometry.

In yet another embodiment, the process of the invention can be used to genotype a subject. In a preferred embodiment, the subject is a recipient or donor of a graft, e.g. an organ or a bone marrow. For example, the process of the invention can be used to determine the identity of major histocompatibility complex (MHC) alleles, e.g., HLA alleles, in a subject. In fact transplantation of a graft to a recipient having different transplantation antigens than the graft will result in rejection of the graft and can also result in graft versus host disease in bone marrow transplantation.

Furthermore, an individual's response to medicaments may be affected by variations in drug modification systems such as cytochrome P450s, and susceptibility to particular infectious diseases may also be influenced by genetic status. Thus, the identification of particular allelic variants can be used to determine a subject's response to specific drugs or infectious diseases. Genes involved in pharmacogenetics are discussed, e.g, in Nora et al., Medical Genetics, fourth Ed. Lea & Febiger Eds.

Some polymorphic regions may not be related to any disease or condition. For example, many loci in at least the human genome contain a polymorphic short tandem repeat (STR) region. Short tandem repeat (STR) loci consist of short, repetitive sequence elements of 3 to 7 base pairs in length. It is estimated there are 200,000 expected trimeric and tetrameric STRs present as frequently as once every 15 kb in the human genome (Edwards et al. 1991b; Beckmann and Weber 1992). Nearly half of the STR loci studied by Edwards et al (1991b) are polymorphic, providing a rich source of genetic markers. Variation in the number of repeat units at a particular locus is responsible for the observed polymorphism reminiscent of VNTR loci (Nakamura et al. 1987) and minisatellite loci (Jeffreys et al. 1985), which contain longer repeat units, and microsatellite or dinucleotide repeat loci (Litt and Luty 1989, Tautz 1989, Weber and May 1989, Beckmann and Weber 1992).

Polymorphic STR loci and other polymorphic regions of genes are extremely useful markers for human identification, paternity and maternity testing, genetic mapping, immigration and inheritance disputes, zygosity testing in twins, tests for inbreeding in man, quality control of human cultured cells, identification of human remains, testing of semen samples, blood stains, and other material in forensic medicine. Such loci are also useful markers in commercial animal breeding and pedigree analysis, and commercial plant breeding. Traits of economic importance in plant crops and animals can be identified through linkage analysis using polymorphic DNA markers. The present invention provides efficient methods for determining the identity of such loci.

STR loci may be amplified via the polymerase chain reaction (PCR) by employing specific primer sequences identified in the regions flanking the tandem repeat. Allelic forms of these loci are differentiated by the number of copies of the repeat sequence contained within the amplified region. Examples of STR loci include: pentanucleotide repeats in the human CD4 locus (Edwards, M. C. et al. (1991) Nucleic Acids Res. 19: 4791); tetranucleotide repeats in the human aromatase cytochrome P-450 gene (CYP19) (Polymeropoulos et al. (1991) Nucleic Acid Res. 19:195); tetranucleotide repeats in the human coagulation factor XIII A subunit gene (F13A1) (Polymeropoulos et al (1991) Nucleic Acids Res. 19:4306); tetranucleotide repeats in the F13Blocus (Nishimura et al (1992) Nucleic Acids Research 20:1167); tetranucleotide repeats in the human C-les/fps proto-oncogene (FES) (Polymeropoulos et al. (1991) Nucleic Acids Research 19: 4018); tetranucleotide repeats in the LFL gene (Zuliani et al. (1990) (Nucleic Acids Research 18:4958); trinucleotide repeats polymorphism at the human pancreatic phospholipase A-2 gene (PLA2) (Polymeropoulos et al (1990) Nucleic Acid Res 18:7468); tetranucleotide repeats polymorphism in the VWF gene (Ploos et al (1990) Nucleic Acids Research 18:4957; and tetranucleotide repeats in the human thyroid peroxidase (hTPO) locus (Anker et al. (1992) Hum. Mol. Genet. 1: 137).

In yet another embodiment, the specific DNA sequence comprises part of a foreign genetic sequence e.g. the genome of an invading microorganism. Non-limiting examples include bacteria and their phages, viruses, fungi, protozoa, and the like. The present methods are particularly applicable when it is desired to distinguish between different variants or strains of a microorganism in order to choose appropriate therapeutic interventions. Examples of disease causing viruses that infect humans and animals and which may be detected by the disclosed processes include: *Retroviridae* (e.g., human immunodeficiency viruses, such as HIV-1 (also referred to as HTLV-III, LAV or HTLV-III/LAV, See Ratner, L. et al., *Nature*, Vol. 313, Pp. 227–284 (1985); Wain Hobson, S. et al, *Cell*, Vol. 40: Pp. 9–17 (1985)); HIV-2 (See Guyader et al., *Nature*, Vol. 328, Pp. 662–669 (1987); European Patent Publication No. 0 269 520; Chakraborti et al., *Nature*, Vol. 328, Pp. 543–547 (1987); and European Patent Application No. 0 655 501); and other isolates, such as HIV-LP (International Publication No. WO 94/00562 entitled *"A Novel Human Immunodeficiency Virus"; Picornaviridae* (e.g., polio viruses, hepatitis A virus, (Gust, I. D., et al., *Intervirology*, Vol. 20, Pp. 1–7 (1983); entero viruses, human coxsackie viruses, rhinoviruses, echoviruses); *Caliviridae* (e.g., strains that cause gastroenteritis); *Togaviridae* (e.g., equine encephalitis viruses, rubella viruses); *Flaviridae* (e.g., dengue viruses, encephalitis viruses, yellow fever viruses); *Coronaviridae* (e.g., coronaviruses); *Rhabdoviridae* (e.g., vesicular stomatitis viruses, rabies viruses); *Filoviridae* (e.g., ebola viruses); *Paramyxoviridae* (e.g., parainfluenza viruses, mumps virus, measles virus, respiratory syncytial virus); *Orthomyxoviridae* (e.g., influenza viruses); *Bungaviridae* (e.g., Hantaan viruses, bunga viruses, phleboviruses and Nairo viruses); Arena viridae (hemorrhagic fever viruses); *Reoviridae* (e.g., reoviruses, orbiviurses and rotaviruses); *Birnaviridae; Hepadnaviridae* (Hepatitis B virus); *Parvoviridae* (parvoviruses); *Papovaviridae* (papilloma viruses, polyoma viruses); *Adenoviridae* (most adenoviruses); *Herpesviridae* (herpes simplex virus (HSV) 1 and 2, varicella zoster virus, cytomegalovirus (CMV), herpes viruses'); *Poxviridae* (variola viruses, vaccinia viruses, pox viruses); and *Iridoviridae* (e.g., African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria sps* (e.g *M. tuberculosis, M avium, M intracellulare, M. kansaii, M gordonae*), *Staphylococcus aureus, Neisseria gonorrhoeae, Neisseria meningitidis, List-* eria monocytogenes, Streptococcus pyogenes (Group A Streptococcus), Streptococcus agalactiae (Group B Streptococcus), Streptococcus (viridans group), Streptococcus faecalis, Streptococcus bovis; Streptococcus (anaerobic sps.), Streptococcus pneumoniae, pathogenic Campylobacter sp., Enterococcus sp., Haemophilus influenzae, Bacillus antracis, corynebacterium diphtheriae, corynebacterium sp., Erysipelothrix rhusiopathiae, Clostridium perfringers, Clostridium tetani, Enterobacter aerogenes, Klebsiella pneumoniae, Pasturella multocida, Bacteroides sp., Fusobacterium nucleatum, Streptobacillus moniliformis, Treponema pallidium, Treponema pertenue, Leptospira, and Actinomyces israelli.

Examples of infectious fungi include: Cryptococcus neoformans, Histoplasma capsulatum, Coccidioides immitis, Blastomyces dermatitidis,Chlamydia trachomatis, Candida albicans. Other infectious organisms (i.e., protists) include: Plasmodium falciparum and Toxoplasma gondii.

The present invention is further illustrated by the following examples which should not be construed as limiting in any way. The contents of all cited references including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and imnology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal,*A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

EXAMPLES

Materials and Methods

Genomic DNA Amplification. Human genomic DNA was extracted using the Qiagen QIAmp Blood Kit following the manufacturer's protocol. A region of the extracted DNA containing the (CAG) repeat associated with SCA I was amplified by the polymerase chain reaction using primers modified to contain a transcription promoter sequence and a region coding for a poly-histidine tail for product purification. The forward primer had the following nucleotide sequence, in which the T7 promoter sequence is italicized (bases on the 5'-side of the promoter are random):

5'd (GAC TTT ACT TGT ACG TGC ATA ATA CGA CTC ACT ATA GGG AGA CTG ACC ATG GGC AGT CTG AGC CA) (SEQ ID NO. 6)

The reverse primer had the following nucleotide sequence, in which the nucleotide sequence encoding the (His)$_6$ tail is represented in bold (the first six 5'-bases are random):

5'd (TGA TTC TCA ATG ATG ATG ATG ATG ATG AAC TTG AAA TGT GGA CGT AC) (SEQ ID NO. 7)

Total reaction volume was 50 μL with 20 pmol primers per reaction. Taq-polymerase including 10×buffer was obtained from Boehringer Mannheim, and dNTPs were obtained from Pharmacia. Cycling conditions were: 5 min at 94° C., followed by 35 cycles of 30 sec at 94° C., 45 sec at 53° C., 30 sec at 72° C., with a final extension time of 2 min at 72° C. PCR products were purified using the Qiagen 'Qiaquick' kit, and elution of the purified products was done with 50 μL 10 mM Trist-HCL buffer (pH 8).

Transcription-Translation: Coupled transcription translation was accomplished using the TNT® T7 Coupled Wheat Germ Extract System from Promega Corp. (CAT# L4140) which includes wheat germ extract; a mixture of all amino acids except methionine, template, RNA polymerase, and the TNT® reaction buffer. Reaction components (50 μL total volume) were thawed and mixed following the manufacturer's protocol using 1 μL of T7 RNA polymerase and 1 pmol of amplified DNA, except that non-labeled methionine was used in place of $^{35}$S radioactive methionine. The reaction mixture was incubated at 30° C. for 90 min.

Polypeptide Purification. The translated histidine-tagged polypeptide was purified from the wheat germ extract mixture using the Qiagen QIAexpress Ni-NTA Protein Purification System following the manufacturer's protocol. Briefly, the extract mixture was washed through (by centrifugation) a spin column containing a nickel-nitriloacetic acid resin which affinity captures the histidine residues of the polypeptide. The polypeptide was then eluted from the column with 100 mM imidazole.

Mass Spectrometry. The translated polypeptide was mixed with matrix either directly from the elution solution, or was lyophilized and resuspended in 5 μL H$_2$O. This solution was mixed 1:1 (v:v) with matrix solution (concentrated sinnapinic acid in 50/50 v:v ethanol/H$_2$O), and 0.5 μL of the mixture was added to a sample probe for analysis in a linear time-of-flight mass spectrometer operated in delayed ion extraction mode with a source potential of 25 kV. Internal calibration was achieved for all spectra using three intense matrix ion signals.

Results

Genomic DNA was obtained from 4 patients having Spinal Cerebellar Ataxia 1 (SCA1), as described above. Each of the patients had 10, 15, and 16 CAG repeats, respectively. The fourth patient had an unknown number of trinucleotide repeats.

A region containing the trinucleotide repeats was PCR amplified using primers hybridizing to sequences located on either side of the repeats and having the nucleotide sequences set forth above. The nucleotide sequence of a PCR product amplified from a region containing 10 CAG repeats is shown in FIG. 1A and the amino acid sequence of a polypeptide encoded by this amplified nucleic acid is shown in FIG. 1B.

The amplified DNA from each of the patients were in vitro transcribed and translated, and the peptides isolated on a Nickel chromatography column, as described above. Mass spectrometric analysis of the peptides encoded by 10, 15, and 16 CAG repeats indicated that these peptides have a molecular mass of 8238.8, 8865.4, and 8993.6 Da, respectively. The polypeptide encoded by the nucleic acid from the fourth patient having an unknown number of trinucleotide repeats has a molecular weight of 8224.8 Da. While this value does not correspond exactly with a unit number of repeats (10 is the closest), it is consistent with detection of a point mutation: the −14 Da shift for this polypeptide corresponds to an Ala−>Gly mutation due to a C−>G DNA mutation. Thus, the process of the invention allows the detection of a single base difference between two nucleic acids.

Detection of such subtle differences in the protein lengths are not reproducibly obtained with electrophoretic methods even with use of multiple internal standards. However, even low performance MS instrumentation is capable of far better than 0.1% mass accuracy in this mass range using internal calibration; higher performance instrumentation such as Fourier transform MS is capable of ppm mass accuracy with internal or external calibration. Note that the mass difference between the 15-and 16-repeat unit polypeptides is 1.4% and the 14 Da mass shift due to the point mutation between the 10-repeat patients is 0.17%; clearly each of these situations can be routinely analyzed successfully.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A process for determining the genetic nature of a phenotype in a subject, comprising the steps of:
   a) obtaining a target nucleic acid molecule from the subject;
   b) preparing a target polypeptide from the nucleic acid molecule;
   c) determining the molecular mass of the target polypeptide by mass spectrometry; and
   d) comparing the target polypeptide with a reference polypeptide of known identity by comparing the molecular mass of the target polypeptide with the molecular mass of the reference polypeptide, thereby identifying an allelic variant of a polymorphic region of a chromosome in the subject.

2. The process of claim 1, wherein the polymorphic region is in a gene.

3. The process of claim 1, wherein the polymorphic region is not in a gene.

4. The process of claim 1, wherein the allelic variant comprises an abnormal number of nucleotide repeats.

5. The process of claim 4, wherein the nucleotide repeats are selected from the group consisting of dinucleotide, trinucleotide, tetranucleotide, and pentanucleotide repeats.

6. The process of claim 4, further comprising quantifying the number of nucleotide repeats.

7. The process of claim 4, wherein the phenotype is associated with a disease or condition, and wherein the nucleotide repeats are trinucleotide repeats.

8. The process of claim 7, wherein the disease or condition is selected from the group consisting of Huntington's disease, prostate cancer, Fragile X syndrome type A, myotonic dystrophy type I, Kennedy disease, Machado-Joseph disease, dentatorubral and pallidolyusian atrophy, spino bulbar muscular atrophy and aging.

9. The process of claim 2, wherein the phenotype is associated with a disease or condition, and wherein the gene is selected from the group consisting of BRCA1, BRCA2, APC, dystrophin gene, β-globin, Factor IX, Factor VIIc, ornithine-d-amino-transferase, hypoxanthine guanine phosphoribosyl transferase, CFTR, p53, and a proto-oncogene.

10. The process of claim 1, wherein the allelic variant is a point mutation.

11. The process of claim 1, wherein the phenotype is responsiveness of the subject to a medicament, and wherein the genetic nature of the phenotype is a polymorphic region of a chromosome associated with responsiveness to the medicament.

12. The process of claim 1, wherein the nucleic acid molecule encoding the target polypeptide comprises nucleotide repeats, and wherein the process is selected from the group consisting of genotyping the subject, forensic analysis, and paternity testing.

13. The process of claim 1, wherein the nucleic acid molecule is a mitochondrial gene.

14. A process for obtaining sequence information or the identity of a plurality of nucleic acid molecules by determining the identities of polypeptides encoded by the nucleic acid molecules, comprising the steps of:
   a) obtaining nucleic acid molecules;
   b) preparing a plurality of polypeptides from the nucleic acid molecules, wherein the plurality of polypeptides include mass modified polypeptides;
   c) determining molecular masses of the differentially mass modified polypeptides by mass spectrometry; and
   d) determining the identities of the polypeptides by comparing the molecular masses of the target polypeptides with the molecular mass of one or more reference polypeptides of known identity, thereby obtaining sequence information or sequence information of the nucleic acid molecules encoding the target polypeptides.

15. The process of claim 14, wherein the polypeptides are obtained by in vitro translation, or by in vitro transcription, followed by translation, of the nucleic acid molecules encoding the polypeptides.

16. The process of claim 14, further comprising, prior to step b), amplifying the nucleic acid molecules encoding the polypeptides.

17. The process of claim 16, wherein amplification is effected using a plurality of pairs of primers, wherein all amplification reactions are effected simultaneously or sequentially at a plurality of annealing temperatures.

18. A process for identifying an individual having spinal cerebellar ataxia-1, comprising detecting an abnormal number of trinucleotide repeats in a nucleic acid molecule obtained from the individual, said trinucleotide repeats comprising CAG trinucleotides and at least one GAG trinucleotide.

19. The process of claim 18, wherein said at least one GAG trinucleotide is detected by detecting a glycine residue encoded by the GAG trinucleotide.

20. The process of claim 19, wherein said glycine residue is detected by mass spectrometry.

21. A process for identifying the presence or absence of a mutation in a target nucleic acid sequence by determining the molecular mass of a polypeptide encoded by the nucleic acid sequence, comprising the steps of:
   a) obtaining a nucleic acid molecule comprising a nucleic acid sequence suspected of containing a mutation;
   b) preparing a polypeptide from a portion of the nucleic molecule comprising the nucleic acid sequence suspected of containing the mutation; and
   c) determining the molecular mass of the polypeptide by mass spectrometry, whereby the molecular mass of the polypeptide identifies the presence or absence of a mutation in the nucleic acid sequence.

22. A process of claim 21, wherein the mutation is an abnormal number of nucleotide repeats, and wherein the molecular mass of the polypeptide identifies the number of nucleotide repeats in the nucleic acid sequence.

23. A process of claim 21, wherein:
   the mutation results in a STOP codon that is identified by a molecular mass of the target polypeptide that is indicative of a truncated polypeptide.

24. A process of claim 21, wherein the identification of a mutation is diagnostic of a genetic disease or a predisposition to a genetic disease.

* * * * *

UNITED STATES PATENT AND TRADEMARK OFFICE
CERTIFICATE OF CORRECTION

PATENT NO.     : 6,207,370 B1
DATED          : March 27, 2001
INVENTOR(S)    : Little et al.

It is certified that error appears in the above-identified patent and that said Letters Patent is hereby corrected as shown below:

<u>Title page,</u>
Item [56], U.S. PATENT DOCUMENTS, add the following citations:

-- 5,324,637    6/1994  Thompson et al. ……..435/68.1
   5,538,897   7/1996  Yates, III et al. …………..436/89 --

FOREIGN PATENT DOCUMENTS, add the following citations:

| -- 02168478 | 6/1986 (GB) | WO 96/36986 | 11/1996 (WO) |
| WO 92/13629 | 9/1992 (WO) | WO 96/36987 | 11/1996 (WO) |
| WO 94/11530 | 5/1994 (WO) | WO 97/08306 | 3/1997 (WO) |
| WO 94/16101 | 7/1994 (WO) | WO 97/16699 | 5/1997 (WO) |
| WO 94/21822 | 9/1994 (WO) | WO 97/37041 | 10/1997 (WO) |
| WO 95/07361 | 3/1995 (WO) | WO 97/42348 | 11/1997 (WO) |
| WO 96/29431 | 9/1996 (WO) | WO 98/11249 | 3/1998 (WO) |
| WO 96/32504 | 10/1996 (WO) | WO 98/20019 | 5/1998 (WO) |
| WO 96/36731 | 11/1996 (WO) | WO 98/20020 | 5/1998 (WO) |
| WO 96/36986 | 11/1996 (WO) | WO 98/20166 | 5/1998 (WO) -- |

-- OTHER PUBLICATIONS, the citation for Hirst et al., replace the existing citation with Hirst et al., Genotype prediction in the Fragile X syndrome, *J. Med. Genet. 28*: 824-829 (1991).; --
"Anderson et al.," replace "(19830." with -- (1983). --;
"Cooper and Krawczak," replace "Mutaion" with -- Mutation --;
"Gust et al.," replace "Invervirology" with -- Intervirology --;
"Guydar et al.," replace "immunodeficienc7y" with -- immunodifficiency --;
"Huse et al.," replace "oa" with -- of --;
"Juhaz et al.," replace "lasewr" with -- laser -- and replace "inoizatio" with -- ionization --;
"McCray et al.," replace "(1992)" with -- (1989) --;
"Yamashita and Fenn ," replace " Phyus." with -- Phys. --; and
"Derwent Abstract," replace "od" with -- of --.

OTHER PUBLICATIONS, add the following citations:

Arlinghaus *et al.*, "Applications of resonance ionization spectroscopy for semiconductor, environmental and biomedical analysis, and for DNA sequencing", *SPIE,* vol. 1435, <u>Opt. Methods Ultrasensitive Detect. Anal. Tech. Appl.</u> pp. 26-35 (1991).;

UNITED STATES PATENT AND TRADEMARK OFFICE
CERTIFICATE OF CORRECTION

PATENT NO. : 6,207,370 B1
DATED : March 27, 2001
INVENTOR(S) : Little et al.

It is certified that error appears in the above-identified patent and that said Letters Patent is hereby corrected as shown below:

OTHER PUBLICATIONS, cont'd,

Beck et al., Applications of dioxetane chemiluminescent probes to molecular biology," Anal. Chem. 62:2258-2270 (1990).;
Beck et al., Chemiluminescent detection of DNA: application for DNA sequencing and hybridization, Nucl Acids Res 17:5115-5123 (1989). Berkenkamp et al., Infrared MALDI mass spectrometry of large nucleic acids, Science 281:260-2 (1998).;
Berkenkamp et al., Infrared MALDI mass spectrometry of large nucleic acids, Science 281:260-2 (1998). Braun et al., Detecting CFTR gene mutations by using primer oligo base extension and mass spectrometry, Clinical Chemistry 43: 1151-1158 (1997).;
Braun et al., Improved Analysis of Microsatellites Using Mass Spectrometry, Genomics 46: 18-23(1997).;
Broude et al. Enhanced DNA sequencing by hybridization, Proc. Natl. Acad. Sci. USA 91:3072-3076 (1994).;
Caldwell et al., Mid-infrared matrix assisted laser desorption ionization with a water/glycerol matrix, Applied Surface Science 127-129:242-247 (1998).;
Chait et al., "Weighing Naked Proteins: Practical, High-Accuracy Mass Measurement of Peptides and Proteins," Science 257: 1885-1894 (1992);
Covey et al., "The determination of protein, oligonucleotide and peptide molecular weights by ionspray mass spectrometry," Rapid Comm in Mass Spect 2(11): 249-256 (1988).;
Crain, "Mass spectrometric techniques in nucleic acid research," Mass Spectr. Rev. 9:505-554 (1990).;
Eckstein (ed.), Oligonucleotides and Analogues, IRL Press, Oxford (1991).;
Edmonds et al., Thermospray liquid chromatography-mass spectrometry of nucleosides and of enzymatic hydrolysates of nucleic acids, Nucleic Acids Research 13:8197-8206 (1985).;
Ehring et al., Photochemical versus thermal mechanisms in matrix-assisted laser desorption/ionization probed by back side desorption, Rapid Comm in Mass Spect 10:821-824 (1996).;
Frank et al., DNA chain length markers and the influence of base composition on electrophoretic mobility of oligodeoxyribonucleotides in polyacrylamide-gels, Nucl Acids Res 6:2069-2087.;
Fu et al., A DNA sequencing strategy that requires only five bases of known terminal sequenece for priming, Proc. Natl. Acad. Sci. USA 92:10162-10166 (1995).;
Fu et al., Efficient preparation of short DNA sequences ladders potentially suitable for MALDI-TOF DNA sequencing, Genetic Analysis 12:137-142 (1996).;
Fu et al., Sequencing double-stranded DNA by strand displacement, Nucl Acids Res 25:677-679 (1997).;

UNITED STATES PATENT AND TRADEMARK OFFICE
CERTIFICATE OF CORRECTION

PATENT NO. : 6,207,370 B1
DATED : March 27, 2001
INVENTOR(S) : Little et al.

It is certified that error appears in the above-identified patent and that said Letters Patent is hereby corrected as shown below:

OTHER PUBLICATIONS, cont'd,

Fu *et al.*, Sequencing exons 5 to 8 of the p53 gene by MALDI-TOF mass spectrometry, Nat Biotechnol 16:381-4 (1998).;
    Gross *et al.*, Investigations of the metastable decay of DNA under ultraviolet matrix-assisted laser desorption/ionization conditions with post-source-decay analysis and hydrogen/deuterium exchange, J Amer Soc for Mass Spect 9:866-878 (1998).;
    Gruić-Sovulj I. *et al.*, Matrix-assisted laser desorption/ionisation mass spectrometry of transfer ribonucleic acids isolated from yeast, Nucleic Acids Res. 25(9):1859-61 (1997).;
    Haglund *et al.*, Marix-assisted laser-desorption mass spectrometry of DNA using an infrared free-electron laser, SPIE 1854:117-128.;
    Hillenkamp and Ehring, Laser desorption mass spectromtrey Part 1: Basic mechanisms and techniques, Mass Spectrometry in the Biological Sciences: A tutorial, pp. 165-179 (1992).;
    Hsiung *et al.*, A new simpler photoaffinity analogue of peptidyl rRNA, Nucl Acids Res 1:1753-1762 (1974).;
    Huth-Fehre *et al.*, Matrix-assisted laser desorption mass spectrometry of oligodeoxythymidylic acids, Rapid Comm in Mass Spect 6:209-213 (1992).;
    Jacobson, *et al.*, Applications of mass spectrometry to DNA sequencing, GATA 8:223-229 (1991).;
    Jurinke *et al.*, Analysis of ligase chain reaction products via matrix-assisted laser desorption/ionization time-of-flight-mass spectrometry, Analy Biochem 237:174-181 (1996).;
    Jurinke *et al.*, Application of nested PCR and mass spectrometry for DNA-based virus detection: HBV-DNA detected in the majority of isolated anti-HBc positive sera, Genetic Analysis 14:97-102 (1998).;
    Jurinke *et al.*, Detection of hepatitis B virus DNA in serum samples via nested PCR and MALDI-TOF mass spectrometry, Genetic Analysis 13:67-71 (1996).;
    Jurinke *et al.*, Recovery of nucleic acids from immobilized biotin-streptavidin complexes using ammonium hydroxide and applications in MALDI-TOF mass spectrometry, Anal. Chem. 69:904-910 (1997).;
    Kirpekar *et al.*, DNA sequence analysis by MALDI mass spectrometry, Nucleic Acids Res. 26:2554-9 (1998).;
    Köster *et al.*, A strategy for rapid and efficient DNA sequencing by mass spectrometry, Nature Biotech 14:1123-1128 (1996).;

UNITED STATES PATENT AND TRADEMARK OFFICE
CERTIFICATE OF CORRECTION

PATENT NO.     : 6,207,370 B1
DATED          : March 27, 2001
INVENTOR(S)    : Little et al.

It is certified that error appears in the above-identified patent and that said Letters Patent is hereby corrected as shown below:

OTHER PUBLICATIONS, cont'd,

Köster et al., N-ACYL proecting groups for deoxynucleosides, A quantitative and comparative study, Tetrahedron 37:363-369 (1981).;
Köster et al., Oligonucleotide synthesis and multiplex DNA sequencing using chemiluminescent detection, Nucl Acids Res 24: 318-321 (1991).;
Köster et al., Polymer support oligonucleotide synthesis--$XV^{1,2}$, Tetrahedron 40:102-112 (1984).;
Köster et al., Some improvements in the synthesis of DNA of biological interest, Nucl Acids Res 7:39-59 (1980).;
Köster et al., Well-defined insoluble primers for the enzymatic synthesis of oligo- and polynucleotides, Hoppe-Seyler's Z. Physiol. Chem. 359:11579-1589 (1978).;
Lawrance et al., Megabase-scale mapping of the HLA gene complex by pulsed field gel electrophoresis, Science 235:1387-1389 (1987);
Li et al., High-Resolution MALDI Fourier Transform Mass Spectrometry of Oligonucleotides, Anal Chem 68:2090-2096 (1996).;
Little et al., Detection of RET proto-oncogene codon 634 mutations using mass spectrometry, J. Mol Med. 75:745-750 (1997).;
Little et al., Direct detection of synthetic and biologically generated double-stranded DNA by MALDI-TOF MS, J. Mass Spec 17:1-8 (1997).;
Little et al., Identification of apolipoprotein E polymorphisms using temperature cycled primer oligo base extension and mass spectrometry, Short Communication.;
Little et al., MALDI on a chip: analysis of arrays of low-femtomole to subfemtomole quantities of synthetic oligonucleotides and DNA diagnostic products dispensed by a piezoelectric pipet, Anal Chem 69:4540-4546 (1997).;
Little et al., Mass spectrometry from miniaturized arrays for full comparative DNA analysis, Nature Med 3:1413-1416 (1997).;
Little et al., Verification of 50- to 100-mer DNA and RNA sequences with high-resolution mass spectrometry, Proc. Natl. Acad. Sci. USA 92:2318-2322 (1995).;
McLafferty, Fred W., "High-Resolution Tandem FT Mass Spectrometry Above 10kDa,"Acc. Chem. Res. 27(11): 379-386 (1994).;
Monforte and Becker, High-throughput DNA analysis by time-of-flight mass spectrometry, Nature Medicine 3:360-362 (1997).;
Mosca et al., HB ABRUZZO [$\beta$143(H21)HIS->ARG] identified by mass spectrometry and DNA analysis, Hemoglobin 17(3):261-268 (1993).;
Nordhoff et al., Ion stablility of nucleic acids in infrared matrix-assisted laser desorption/ionization mass spectrometry, Nuc Acids Res. 21:3347-3357 (1993).

UNITED STATES PATENT AND TRADEMARK OFFICE
CERTIFICATE OF CORRECTION

PATENT NO. : 6,207,370 B1
DATED : March 27, 2001
INVENTOR(S) : Little et al.

It is certified that error appears in the above-identified patent and that said Letters Patent is hereby corrected as shown below:

OTHER PUBLICATIONS, cont'd,

Nordoff *et al.*, Matrix-assisted laser desorption/ionization mass spectrometry of nucleic acids with wavelength in the ultraviolet and infrared, Rapid Comm. Mass Spect 6:771-776 (1992).;

O'Donnell *et al.*, High-density, covalent attachment of DNA to siliocn wafers for analysis by MALDI-TOF mass spectrometry, Analytical Chemistry 69:2438-2443 (1997).;

O'Donnell *et al.*, MassArray as an enabling technology for the industrial-scale analysis of DNA, Genetic Engineering News 17 (1997).;

O'Donnell-Maloney *et al.*, Microfabrication and array technologies for DNA sequencing and diagnostics, Genetic Analysis: Biomolecular Engineering 13:151-157 (1996).;

Overberg *et al.*, Laser Desorption Mass Spectrometry. Part II Performance and Applications of Matrix-Assisted Laser Desorption/Ionization of Large Biomolecules, "Mass Spectrometry in the Biological Science: A Tutorial 181-197 (1992).;

Pieles *et al.*, Matrix-assisted laser desorption ionization time-of-flight mass spectrometry: a powerful tool for the mass and sequence analysis of natural and modified oligonucleotides, Nucleic Acids Res. 21:3191-3196 (1993).;

Pomerantz *et al.*, Determination of oligonucleotide composition from mass spectrometrically measured molecular weight, Am. Soc. Mass Spectrom. 4:204-09 (1993).;

Prome *et al.*, Use of combined mass spectrometry methods for the characterization of a new variant of human hemoglobin: The double mutant hemoglobin villeparisis beta 77(EF1), J. American Society for Mass Spect 7(2):163-167 (1996).;

Ruppert *et al.*, A filtration method for plasmid isolation using microtiter filter plates, Anal. Biochem. 230:130-134 (1995).;

Ruppert *et al.*, A rapid and high throughput method for plasmid isolations, Presented: Automation in Mapping and DNA Sequencing Conference, Aug.31 - Sept. 2 1994.;

Ruppert *et al.*, Preparation of plasmid DNA as sequencing templates in a microtiter plate format, Paper presented, Cold Spring Harbor Laboratory.;

Schram, Mass spectrometry of nucleic acid componenents, Biomed. App. Mass Spectrom. 34:203-287 (1990).;

Sequenom Reports On Use of Its DNA MassArray™ Technology to Analyze Genes Associated with Alzheimer's Disease and Arteriosclerosis: Technology Has Applications in Drug Development, Press Release: Sept. 22, 1997, http://www.sequenom.com/pressrelease.htm.;

UNITED STATES PATENT AND TRADEMARK OFFICE
CERTIFICATE OF CORRECTION

PATENT NO. : 6,207,370 B1
DATED : March 27, 2001
INVENTOR(S) : Little et al.

It is certified that error appears in the above-identified patent and that said Letters Patent is hereby corrected as shown below:

OTHER PUBLICATIONS, cont'd,

Sequenom Advances the Industrial Genomics Revolution with the launch of Its DNA MassArray™ Automated Process Line, Press Release: Sept. 28, 1998, http://www.sequenom.com/pressrelease.htm.;
    Sequenom Reports DNA MassArray™ Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.;
    Sequenom Signs Agreement With Bruker-Franzen Analytik to Develop Mass Spectrometer for DNA Massarray Analysis, Press Release: Jan. 12, 1998, http://www.sequenom.com/pressrelease.htm.;
    Sequenom Uses DNA MassArray™ to Sequence Section of Human Cancer-Related p53 Gene", Press Release: Mar. 27, 1998, http://www.sequenom.com/pressrelease.htm.;
    Shaler *et al.*, Effect of Impurities on the matrix-assisted laser desorption mass spectra of single-stranded oligodeoxynucleotides, Anal. Chem. 68:576-579 (1996).;
    Siegert *et al.*, Matrix-assisted laser desorption/ionization time-of-flight mass spectrometry for the detection of polymerase hain reaction products containing 7-deasapurine moieties, Anal. Biochem. 243:55-65 (1996).;
    Sinha *et al.*, $\beta$-cyanoethyl N, N-dialkylamino/N-morpholinomonochloro phosphoamidites, new phosphitylating agents facilitating ease of deprotection and work-up of synthesized oligonucleotides, Tetrahedron Lett. 24:5843-5846 (1983).;
    Sinha *et al.*, Polymer support oligonucleotide synthesis XVIII: Use of B-cyanoethyl-N, N-dialkylamino-/N-morpholino phosphoramidite of deoxynucleosides for the synthesis of DNA fragments simplifying deprotection and isolation of final product, Nucleic Acids Res. 12:4539 (1984).;
    Siuzdak, The emergence of mass spectrometry in biochemical research, Proc. Natl. Acad. Sci. USA 91:11290-11297 (1994).;
    Smith *et al.*, Capillary zone electrophoresis-mass spectrometry using an elctrospray ionization interface, Anal. Chem. 60:436-441 (1988).;
    Sproat *et al.*, The synthesis of protected 5'-amino-2',5'-dideoxy-ribonucleoside-3'-O-phosphoramidites; applications of 5'-aminooligo-deoxyribo-nucleotides, Nucleic Acids Res. 15:6181-6196 (1987).;

UNITED STATES PATENT AND TRADEMARK OFFICE
CERTIFICATE OF CORRECTION

PATENT NO.    : 6,207,370 B1
DATED         : March 27, 2001
INVENTOR(S)   : Little et al.

It is certified that error appears in the above-identified patent and that said Letters Patent is hereby corrected as shown below:

OTHER PUBLICATIONS, cont'd,

Tang, *et al.*, Improving mass resolution in MALDI/TOF analysis of DNA, American Society of Mass Spectrometrists Conference: May 21 to 26, 1995.;
    Tang, *et al.*, Matrix-assisted laser desorption/ionization mass spectrometry of immobilized duplex DNA probes, Nucleic Acids Research 23:3126-3131 (1995).;
    Wu *et al.*, Matrix-assisted Laser Desorption Time-of-flight Mass Spectrometry of Oligonucleotides Using 3-Hydroxypicolinic Acid as an Ultraviolet-sensitive Matrix, Rapid Comm Mass Spec 7:142-146 (1993).;
    Wu *et al.*, Time-of-Flight Mass Spectrometry of Underivatized Single-Stranded DNA Oligomers by Matrix-Assisted Laser Desorption, Anal. Chem. 66:1637-1645 (1994).; and
    Yamashita *et al.* "Electrospray ion source. Another variation on the free-jet theme," *J. Phys. Chem.* 88:4451-4459, (1984). --

Column 20,
Line 34, replace "or" with -- of --;

Column 21,
Line 20, replace "nbosome" with -- ribosome --; and

Column 25,
Line 27, replace "imnology" with -- immunology --.

Signed and Sealed this

Thirteenth Day of May, 2003

JAMES E. ROGAN
*Director of the United States Patent and Trademark Office*